(12) United States Patent
Patterson et al.

(10) Patent No.: US 9,857,315 B2
(45) Date of Patent: Jan. 2, 2018

(54) FOURIER TRANSFORM MICROWAVE SPECTROSCOPY FOR ENANTIOMER-SPECIFIC DETECTION OF CHIRAL MOLECULES

(71) Applicant: President and Fellows of Harvard College, Cambridge, MA (US)

(72) Inventors: David S. Patterson, Somerville, MA (US); John M. Doyle, Belmont, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 236 days.

(21) Appl. No.: 14/415,211

(22) PCT Filed: Mar. 14, 2013

(86) PCT No.: PCT/US2013/031779
§ 371 (c)(1),
(2) Date: Jan. 16, 2015

(87) PCT Pub. No.: WO2014/014512
PCT Pub. Date: Jan. 23, 2014

(65) Prior Publication Data
US 2015/0177164 A1    Jun. 25, 2015

Related U.S. Application Data

(60) Provisional application No. 61/673,917, filed on Jul. 20, 2012, provisional application No. 61/761,582, filed on Feb. 6, 2013.

(51) Int. Cl.
| | |
|---|---|
| G01N 27/416 | (2006.01) |
| H01S 3/30 | (2006.01) |
| G01N 22/00 | (2006.01) |

(52) U.S. Cl.
CPC .................... *G01N 22/00* (2013.01)

(58) Field of Classification Search
CPC ....................................................... G01N 22/00
(Continued)

(56) References Cited

U.S. PATENT DOCUMENTS

| | | |
|---|---|---|
| 3,889,182 A | 6/1975 | Easley et al. |
| 3,973,186 A | 8/1976 | Uehara et al. |

(Continued)

FOREIGN PATENT DOCUMENTS

WO    WO-2010/031387    3/2010

OTHER PUBLICATIONS

Brown et al., "A broadband Fourier transform microwave spectrometer based on chirped pulse excitation", Review of Scientific Instruments, vol. 79, No. 5, May 9, 2008, pp. 53103-1 to 53103-13.

(Continued)

*Primary Examiner* — Farhana Hoque
(74) *Attorney, Agent, or Firm* — Foley & Lardner LLP; Cliff Z. Liu

(57) ABSTRACT

A spectrometer includes: (1) a housing defining a volume into which an analyte gas is introduced, the analyte gas including a chiral component; (2) a microwave generator coupled to the housing and configured to apply a microwave pulse to the analyte gas, the microwave pulse being polarized along a first direction; (3) an electric field generator coupled to the housing and configured to apply a switched electric field to the analyte gas, the electric field being oriented along a second direction different from the first direction; (4) a phase-sensitive microwave detector coupled to the housing and configured to detect an induced microwave emitted by the analyte gas, the induced microwave being polarized along a third direction different from the first direction and the second direction; and (5) an analyzer coupled to the phase-sensitive microwave detector and configured to detect an enantiomer of the chiral component based on a phase of the induced microwave.

20 Claims, 22 Drawing Sheets

(58) Field of Classification Search
USPC .................................. 324/438, 639; 372/5
See application file for complete search history.

(56) References Cited

U.S. PATENT DOCUMENTS

| | | | |
|---|---|---|---|
| 5,057,782 | A | 10/1991 | Brown et al. |
| 5,063,391 | A | 11/1991 | Jaggard et al. |
| 5,548,217 | A * | 8/1996 | Gibson .................... A61L 2/24 |
| | | | 324/313 |
| 5,831,439 | A | 11/1998 | Suenram et al. |
| 7,301,633 | B2 | 11/2007 | Gibbs et al. |
| 7,911,608 | B2 | 3/2011 | Busch et al. |
| 2007/0284241 | A1 | 12/2007 | Kibar |
| 2009/0296744 | A1 * | 12/2009 | Dantus ................... G01N 21/21 |
| | | | 372/5 |

OTHER PUBLICATIONS

Extended European Search Report issued on EP Application 13819984.9, dated Jan. 26, 2016.
Grubbs et al., "Chirped-Pulse fourier transform microwave spectroscopy of the simple chiral compound bromofluoroacetonitrile, CHBrFCN," Journal of Molecular Spectroscopy, vole 258, No. 1-2, Aug. 23, 2009, pp. 1-5.
Lesarri et al., "Confirmation of chiral molecules: The rotational spectrum of 2-chloropropionic acid," Chemical Physics Letters, vol. 468, No. 1-3, Nov. 27, 2008, pp. 18-22.
Velino et al., "Conformational Equilibria in Diols: The Rotational Spectrum of Chiral 1,3-Butandiol," The Journal of Physical Chemistry, vol. 115, No. 34, Mar. 18, 2011, pp. 9585-9589.
Grubbs II et al.; "Chirped-pulse fourier transform microwave spectroscopy of the simple chiral compound bromofluoroacetonitrile, CHBrFCN"; Journal of Molecular Spectroscopy, Aug. 23, 2009; vol. 258, pp. 1-5.
International Preliminary Report on Patentability for PCT/US2013/031779, dated Jan. 20, 2015.
ISR & Written Opinion dated Jun. 28, 2013; PCT/US2013/031779; President and Fellows of Harvard College et al.
King et al., "A microwave study of the hetero-chiral dimer of butan-2-ol," Chemical Physics Letters 348, Nov. 9, 2001, pp. 343-349.
Notice of rejection for Japanese Patent Application No. 2016-133791, dated Jul. 19, 2017, 7 pgs.
Sumiyoshi, "Wideband Fourier-Transform Microwave Spectroscopy Using Chirped Pulse," Bunko Kenkyu (Spectro-research), Feb. 15, 2013, 62(1), 6 pgs.

* cited by examiner

FOURIER TRANSFORM MICROWAVE SPECTROSCOPY FOR ENANTIOMER-SPECIFIC DETECTION OF CHIRAL MOLECULES

CROSS REFERENCE TO RELATED APPLICATIONS

This application is a national stage application of International Application Serial No. PCT/US2013/031779, filed on Mar. 14, 2013, which claims the benefit of U.S. Provisional Application No. 61/673,917, filed on Jul. 20, 2012, and the benefit of U.S. Provisional Application No. 61/761,582, filed on Feb. 6, 2013, the disclosures of which are incorporated herein by reference in their entirety.

STATEMENT REGARDING FEDERALLY SPONSORED RESEARCH OR DEVELOPMENT

This invention was made with Government support under Grant No. PHY-0855575, awarded by the National Science Foundation. The government has certain rights in this invention.

FIELD OF THE INVENTION

This disclosure generally relates to spectroscopy techniques and, more particularly, spectroscopy techniques for discriminating between enantiomers of chiral molecules.

BACKGROUND

Many molecules can exist as stable right-handed or left-handed enantiomers, which can be referred as R- and S-enantiomers. Although such molecules can have substantially identical physical and chemical properties in a symmetric environment, the molecules can have quite different chemical properties when interacting with other chiral molecules. This can be of great importance in biological systems, as the physiological effect of drugs and other biologically active molecules can vary significantly between enantiomers. There is, therefore, considerable interest in a general, sensitive technique for enantiomer-specific chemical detection.

It is against this background that a need arose to develop the embodiments described herein.

SUMMARY

Some embodiments of this disclosure relate to extensions of Fourier transform microwave (FTMW) spectroscopy to provide a general, sensitive, enantiomer-specific detection technique for polar chiral molecules. In some implementations, the extensions can be viewed as a version of three wave mixing, by exploiting resonance enhancement in chiral gases with relatively long (e.g., several µs typical) decoherence times. Enantiomers can be distinguished by encoding a chirality-dependent complex Rabi frequency of electric dipole transitions onto a phase of emitted radiation. The extreme selectivity of rotational resonances allows the technique to identify enantiomers even amid a complex mixture, including a mixture that includes many other chiral compounds—a situation applicable for many real world samples. The technique can be applied to any gas-phase asymmetric top molecule with non-zero electric dipole moments $\mu_a$, $\mu_b$, and $\mu_c$.

Embodiments of this disclosure include enhancements of Balle-Flygare type and chirped pulse (CP)-FTMW type spectrometers, including spectrometers using vapor cells, supersonic jets, and buffer gas cooling-based sources of cold molecules. In some implementations, broadband, enantiomer-specific resolution of a complex mixture can be achieved at the level of one part per thousand or one part per ten thousand (or even lower concentrations) and in a few minutes of integration. Enantiomer-specific sensitivities at the part per million level for single mixture components can be achieved in resonantly enhanced Balle-Flygare-type spectrometers of some implementations.

In one embodiment, a spectrometer includes: (1) a housing defining a volume into which an analyte gas is introduced, the analyte gas including a chiral component; (2) a microwave generator coupled to the housing and configured to apply a microwave pulse to the analyte gas, the microwave pulse being polarized along a first direction; (3) an electric field generator coupled to the housing and configured to apply a switched electric field to the analyte gas, the electric field being oriented along a second direction different from the first direction; (4) a phase-sensitive microwave detector coupled to the housing and configured to detect an induced microwave emitted by the analyte gas, the induced microwave being polarized along a third direction different from the first direction and the second direction; and (5) an analyzer coupled to the phase-sensitive microwave detector and configured to detect an enantiomer of the chiral component based on a phase of the induced microwave.

In another embodiment, a spectrometer includes: (1) a housing defining a volume into which an analyte gas is introduced, the analyte gas including a chiral component; (2) a microwave generator coupled to the housing and configured to apply a microwave pulse to the analyte gas, the microwave pulse configured to induce a first polarization along a first direction; (3) an electric field generator coupled to the housing and configured to apply a switched electric field to the analyte gas, the electric field configured to induce a second polarization along a second direction different from the first direction; (4) a set of microwave detectors coupled to the housing and configured to detect the first polarization and the second polarization; and (5) an analyzer coupled to the set of microwave detectors and configured to detect a chirality of the chiral component based on a phase of the second polarization.

In a further embodiment, a spectrometer includes: (1) a housing defining a volume into which an analyte gas is introduced, the analyte gas including a chiral component; (2) a first generator coupled to the housing and configured to apply a first pulse to the analyte gas, the first pulse being polarized along a first direction; (3) a second generator coupled to the housing and configured to apply a second pulse to the analyte gas, the second pulse being polarized along a second direction different from the first direction; (4) a phase-sensitive detector coupled to the housing and configured to detect an induced radiation emitted by the analyte gas, the induced radiation being polarized along a third direction different from the first direction and the second direction; and (5) an analyzer coupled to the phase-sensitive detector and configured to detect an enantiomer of the chiral component based on a phase of the induced radiation.

Other aspects and embodiments of this disclosure are also contemplated. The foregoing summary and the following detailed description are not meant to restrict the disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Definitions

The following definitions apply to some of the aspects described with respect to some embodiments of this disclosure. These definitions may likewise be expanded upon herein.

As used herein, the singular terms "a," "an," and "the" include plural referents unless the context clearly dictates otherwise. Thus, for example, reference to an object can include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

Enantiomer-Specific Detection of Chiral Molecules

Figure 1:
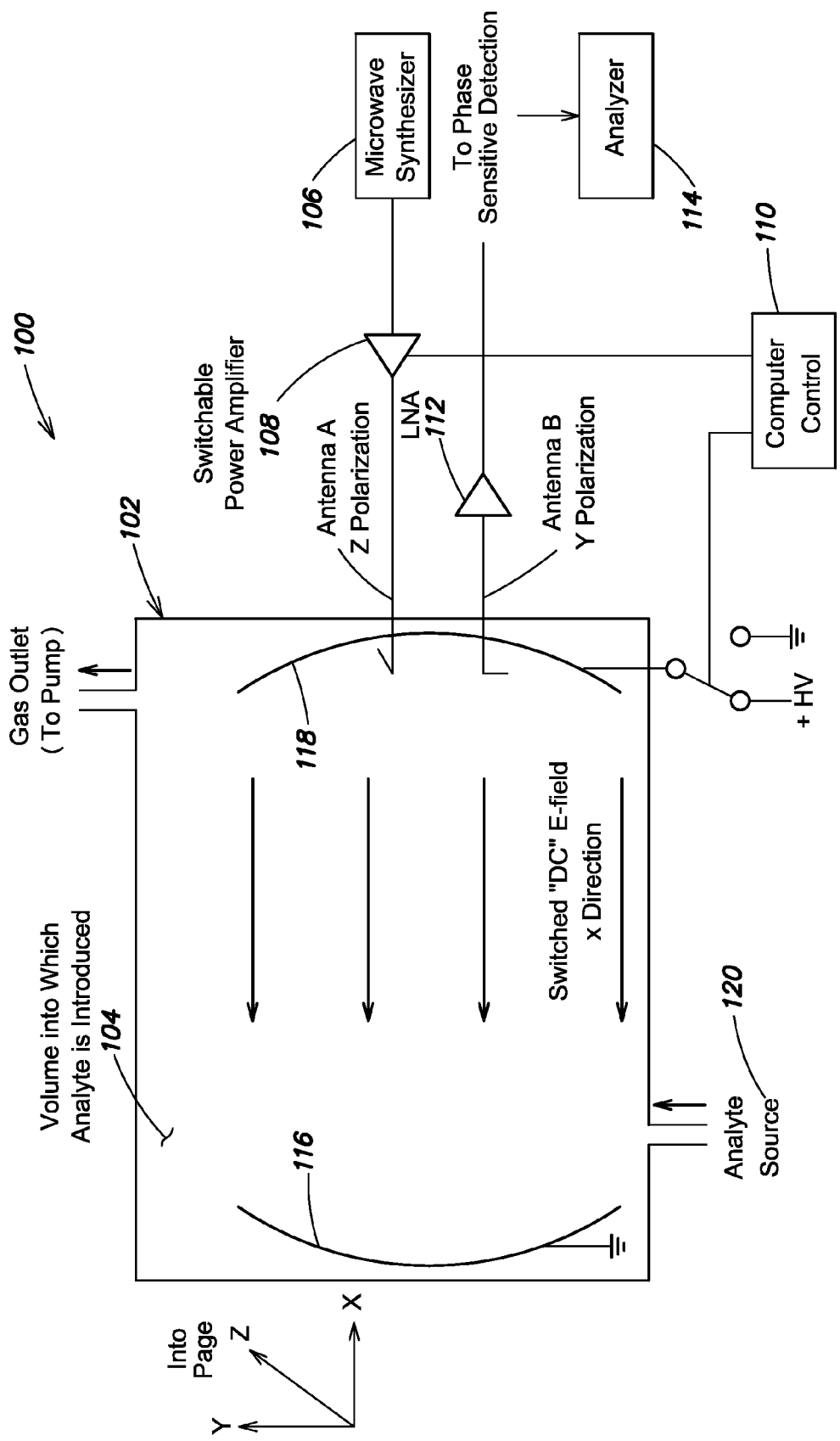
FIG. 1: A Balle-Flygare type spectrometer enhanced to provide enantiomer-specific detection. Molecules are polarized initially in the z direction via a pulse from an antenna A, which also can be used for "traditional" FTMW identification of the molecules; enantiomers are distinguished via phase-sensitive detection from an antenna B, which is oriented to detect y-polarized microwaves. A relatively strong electric field oriented in the x direction can turned on or off.

FIG. 1 shows an apparatus 100 configured to identify chiral molecules in a mixture, according to an embodiment of this disclosure. The apparatus 100 is configured as a FTMW spectrometer, and includes a housing 102 that defines a volume 104 into which a mixture, referred as an analyte, can be introduced from an analyte source 120. The analyte is a gas mixture including one or more a-priori unknown polar components. The apparatus 100 is configured to measure the concentration of each enantiomer of a particular species in the analyte. The two enantiomers of species X can be referred as R-X and S-X.

The apparatus 100 operates according to an extension of techniques of FTMW spectroscopy as described further below. This extension can be referred as an enantiomer-dependent, one-color Stark FTMW spectroscopy in some implementations. In effect, an enantiomer-dependent sign of a complex Rabi frequency can be transferred into a sign or phase of a real observable, in this case an ensemble polarization and hence the phase of induced radiation.

Specifying a molecule's three rotational constants, A, B, and C, and three corresponding dipole moments, $\mu_a$, $\mu_b$, and $\mu_c$, can be sufficient to specify the molecule's chirality. Reversing the sign of any one of $\mu_a$, $\mu_b$, and $\mu_c$ typically results in a description of the opposite enantiomer. In some implementations, axes can be defined such that one enantiomer has all of $\mu_a$, $\mu_b$, and $\mu_c$ positive, and the other has all of $\mu_a$, $\mu_b$, and $\mu_c$ negative. Axes also can be chosen such that $\mu_a$ and $\mu_b$ are positive for both enantiomers, so the R- and S-enantiomers are distinguished by the sign of $\mu_c$. In either case, the sign of $\mu_a\mu_b\mu_c$ changes between enantiomers. The techniques described here can be generally applied to any gas-phase asymmetric top molecule with nonzero $\mu_a$, $\mu_b$, and $\mu_c$, encompassing a broad range of relatively complex molecules that can be vaporized.

The energy levels and rotational transition strengths of a molecule interacting with an electric field typically depend on A, B, C and the absolute value of the dipole moments, $|\mu_a|$, $|\mu_b|$, and $|\mu_c|$. Measurements of these levels or transitions strengths therefore typically cannot determine the chirality of the molecule. In contrast, a complex Rabi frequency representing electric dipole transitions between chiral states can differ in sign for opposite enantiomers. By exploiting a 3-level system where electric dipole transitions are allowed on most or all transitions, this complex Rabi frequency and, hence, an enantiomer can be determined from a phase of a (real) macroscopic oscillating electric field produced by a molecular ensemble.

As illustrated in FIG. 1, the apparatus 100 also can be used for "traditional" FTMW identification of molecules. Traditional FTMW techniques can identify polar gas phase molecules in a mixture, but generally cannot distinguish which enantiomer is present: the signals from pure R-X, pure S-X, or a racemic mixture can be indistinguishable.

In traditional FTMW spectroscopy, an analyte gas is exposed to a short, intense microwave pulse $P_1$ of linearly polarized microwaves from an antenna A. In some implementations, the pulse $P_1$ is substantially monochromatic, although deviations from monochromaticity are also contemplated. The pulse $P_1$ is generated by a microwave synthesizer 106 and amplified by a switchable amplifier 108. Another polarized microwave source or generator can be used in place of, or in combination with, the microwave synthesizer 106 and the switchable amplifier 108. The intensity and frequency of this pulse are such that a population of molecules of either R-X or S-X in a given state |f> will be partially polarized by driving the molecules into a superposition of the state |f> and a connected state |g>. The molecules will then produce an oscillating electric field $\in_1$ at a frequency $v_{fg}$, and this field is collected by the antenna A and recorded or otherwise processed, typically via phase-sensitive heterodyne detection techniques. This radiation persists for a decoherence time $\tau_{decoh}$, after which the molecules are re-thermalized via collisions, and the experiment can be repeated. $\tau_{decoh}$ typically varies from about $10^{-3}$ to $10^{-5}$ seconds in traditional FTMW spectroscopy. In a typical application, many iterations of the experiment can be averaged in order to achieve a higher sensitivity. Analyte molecules can be identified because each species of molecules radiates in a characteristic set of frequencies, corresponding to allowed transitions $v_{fg}$ for various $|f\rangle$ and $|g\rangle$. In traditional FTMW spectroscopy, R-X and S-X generally radiate at the same frequencies and thus cannot be distinguished. Another microwave detector, such as a phase-sensitive microwave detector, can be used in place of, or in combination with, the antenna A.

For enantiomer-specific detection, the apparatus 100 is configured to switch on or off an electric field $E_x$ that is applied to the volume 104 of molecules polarized by $P_1$. The field $E_x$ is switched on or off after the pulse $P_1$ (e.g., after the end, the peak, or a majority or substantial fraction of $P_1$) and before the time when the radiation is collected; the field therefore should be switched faster than the decoherence time $\tau_{decoh}$. $E_x$ is substantially orthogonal to the polarization of $P_1$ in the illustrated embodiment. This switched electric field induces a second oscillating electric field $\in_2$ at a frequency $v_{fg}$, with this second field $\in_2$ substantially orthogonal to both $P_1$ and $E_x$. $\in_2$ is collected by a second antenna, namely antenna B, and recorded or otherwise processed along with $\in_1$. The sign (or phase) and the magnitude of $\in_2$ are extracted to provide a quantitative indicator of enantiomeric excess. The sign of the field $\in_2$ induced by R-X is substantially opposite the sign of $\in_2$ induced by S-X. Stated in another way, the phase of the field $\in_2$ is shifted by about $\pi$ radians between R-X and S-X, and indicates a dominant enantiomer (e.g., the sign of the enantiomeric excess). The magnitude of the induced field $\in_2$ indicates an extent of the enantiomeric excess. $\in_2$ approaches zero if R-X and S-X are present in equal amounts. The electric field $E_x$ is applied by a voltage source +HV, and is switched by a controller 110. Another electric field source or generator can be used in place of, or in combination with, the voltage source +HV and the controller 110. Enantiomers R-X and S-X are distinguished via phase-sensitive detection from the antenna B, which is oriented to detect y-polarized microwaves that are conveyed to a low noise amplifier (LNA) 112. The LNA 112 is isolated from the polarization pulse due to its orthogonal polarization, which can remove the requirement for a protection switch. Processing of the signals from the LNA 112 is carried out by an analyzer 114, which can be implemented in hardware, software, or a combination of hardware and software. Another microwave detector, such as a phase-sensitive microwave detector, can be used in place of, or in combination with, the antenna B.

In some implementations, the volume 104 corresponds to a vapor cell held at or around a temperature such that X has a significant vapor pressure (e.g., at or above $10^{-6}$ torr), and a gas is introduced through a valve at a pressure at or below this vapor pressure. In other implementations, the gas is introduced into the volume 104 (corresponding to a vacuum chamber) via a seeded supersonic jet, providing an intense, pulsed source of molecules cooled to a temperature below (e.g., far below) room temperature (e.g., about 1-10 K or about 1-5 K). In yet other implementations, the volume 104 corresponds to a buffer gas cell held at or around cryogenic temperatures, and a gas phase sample of the analyte is introduced via an aperture in the side of the volume 104. Introduction of the analyte into a cryogenic buffer gas cell also can be performed using a thermal beam.

The analyte in the volume 104 is exposed to a short, intense pulse $P_1$ of microwaves, including a component at a frequency $\omega_{fg}=(E(|f\rangle)-E(|g\rangle))/\hbar$, where $|f\rangle$ and $|g\rangle$ are two rotational states of X connected by an allowed electric dipole transition, and $v_{fg}=\omega_{fg}/2\pi$. Pulse $P_1$ is linearly polarized substantially along the z axis. In the discussion below, it is assumed that this allowed transition is a c-type transition, but similar analysis holds for a-type and b-type transitions as well. The intensity and frequency of this pulse is such that typical molecules in the $|f\rangle$ state of either R-X or S-X will experience an approximate $\pi/2$ pulse, leaving the molecules in a state:

$$\Psi_2 = \frac{1}{\sqrt{2}}\left(|f\rangle + \frac{\mu_c}{|\mu_c|}e^{-i(\omega_1 t + \phi_1)}|g\rangle\right)$$

In the above equation, $\omega_1$ is typically set to be substantially equal to $\omega_{fg}$. Before an induced signal can decay, a substantially spatially uniform electric field substantially parallel to the x axis (and substantially orthogonal to $P_1$) is applied. In a system with nonzero $\mu_a$, $\mu_b$, and $\mu_c$, this field will mix the states $|f\rangle$ and $|g\rangle$ with other states that are connected by electric dipole transitions to both of these states. The radiation emitted by this admixed state includes a component polarized along the y axis, namely $\in_2$. $\in_2$ is proportional to $\mu_a\mu_b\mu_c$, and thus changes sign with a particular enantiomer. If both enantiomers of a given species are present in equal amounts, $\in_2$ approaches 0.

Figure 2:
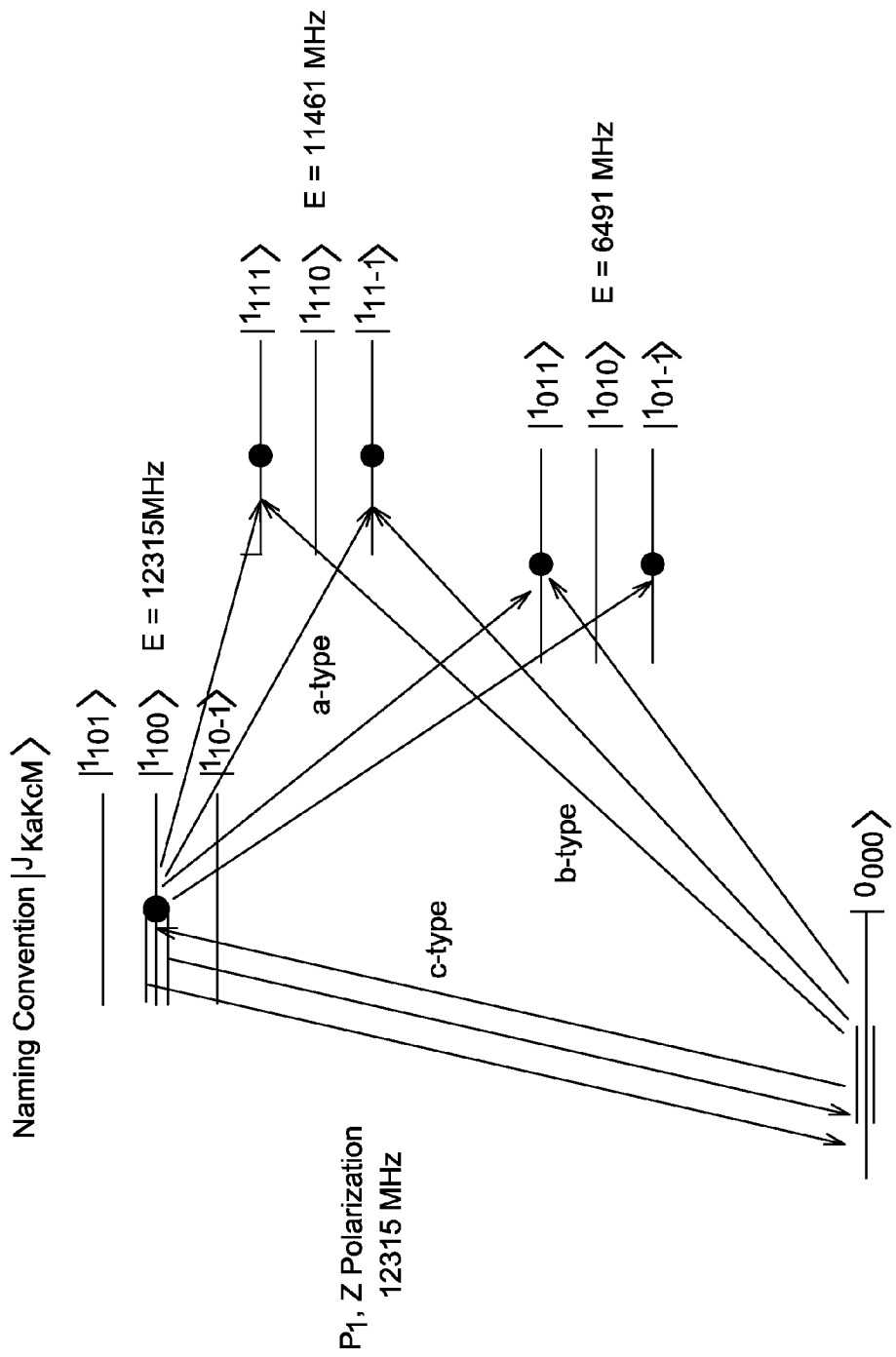
FIG. 2: A chirality-dependent one-color Stark FTMW spectroscopy experiment that discriminates between enantiomers. Levels shown are for 1-2 propanediol.

FIG. 2 shows the level structure relevant to an embodiment of this disclosure, using ground state 1-2 propanediol as an example species. Molecules begin in an absolute rotational ground state, $|0_{000}\rangle$ with no external field. A z-polarized $\pi/2$ pulse at about 12,315 MHz puts the molecules in a superposition of $|0_{000}\rangle$ and $|1_{100}\rangle$ via a c-type transition. An electric field in the x direction is then applied, which mixes these states with $|1_{11M}\rangle$ states via a-type and b-type matrix elements so as to allow previously forbidden y-polarized radiation. The $|1_{01M}\rangle$ manifold also can contribute to the y-polarized radiation, but can be omitted in the analysis for some implementations.

Figure 3:
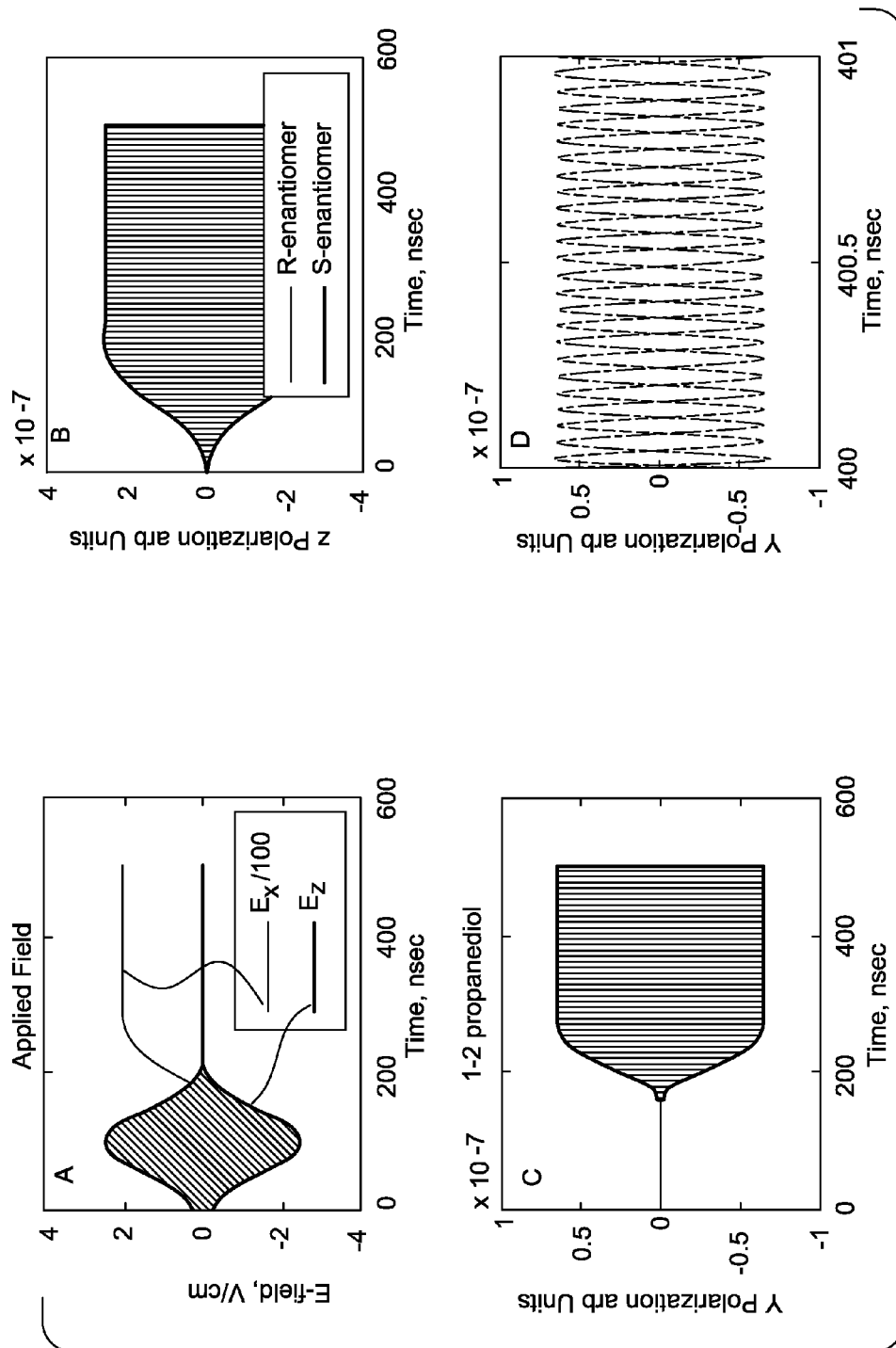
FIG. 3: Quantum simulation of a (hyperfine-free) 1-2 propanediol molecule undergoing chirality dependent one-color Stark FTMW Spectroscopy. A: Applied electric fields in the z (AC) and x (DC) directions. The polarization pulse (shaded) is at about 12,315 MHz, corresponding to $|0_{00}\rangle$ to $|1_{10}\rangle$. B: "Traditional" (i.e., non-chiral) z-polarized free induction decay signal induced by the polarization pulse. C: Free induction decay signal in the y-plane, induced by the DC electric field. D: A magnified version of C, showing the expected enantiomer-dependent phase.
Figure 4:
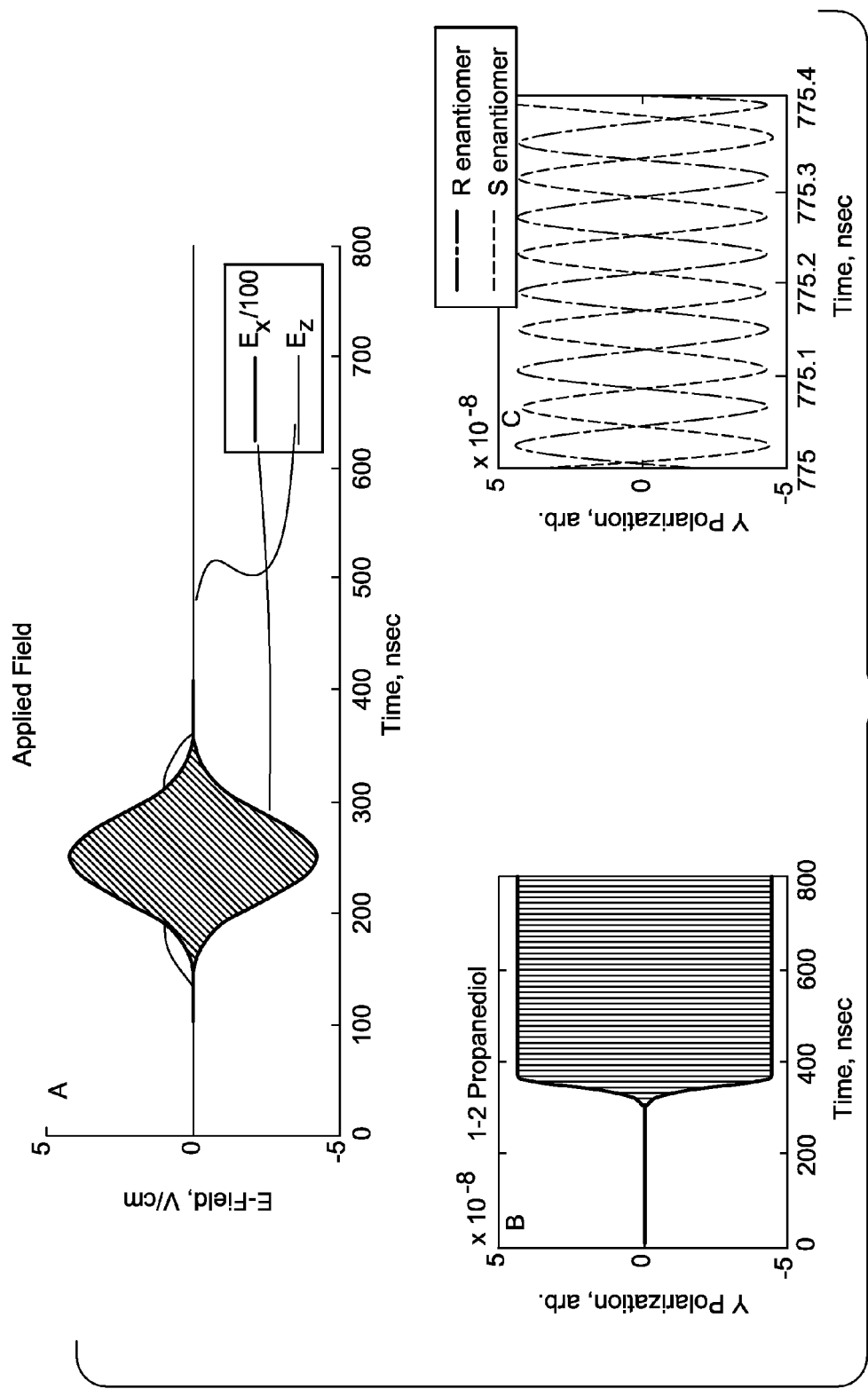
FIG. 4: A simulation of enantiomer-dependent spectroscopy of 1-2 propanediol with experimentally realistic parameters. A: A high voltage pulse along x is applied substantially simultaneously with the z-polarized microwave pulse. B: Turning off the high voltage pulse produces the y-polarized enantiomer-dependent radiation. C: A magnified version of C, showing the expected enantiomer-dependent phase for R- and S-enantiomers.

FIGS. 3 and 4 show results of simulations for enantiomer-specific detection of the chiral molecule 1-2 propanediol. The simulations show that, for applied fields of about 200 V/cm, an expected chirality-dependent y-polarized signal is modestly smaller (e.g., about 8 times smaller) in magnitude than the "traditional" z-polarized free induction decay signal at about 12.32 GHz. At higher J-values, the enantiomer-dependent signal can further diminish as connected levels are further apart and are therefore less efficiently mixed by the DC field. Nevertheless, such signal strengths can be readily detected for sensitive and enantiomer-specific discrimination of chiral species.

In some implementations, an electric field $E_x$ is switched on between a polarization pulse $P_1$ and a detection period. An example timing sequence for such an implementation is shown in FIG. 3A. In other implementations, the electric field $E_x$ is switched on and off substantially simultaneously with the polarization pulse $P_1$ and before the detection period. An example timing sequence for such an implementation is shown in FIG. 4A. In yet other implementations, the electric field $E_x$ is switched off between the polarization pulse $P_1$ and the detection period.

Figure 5A:
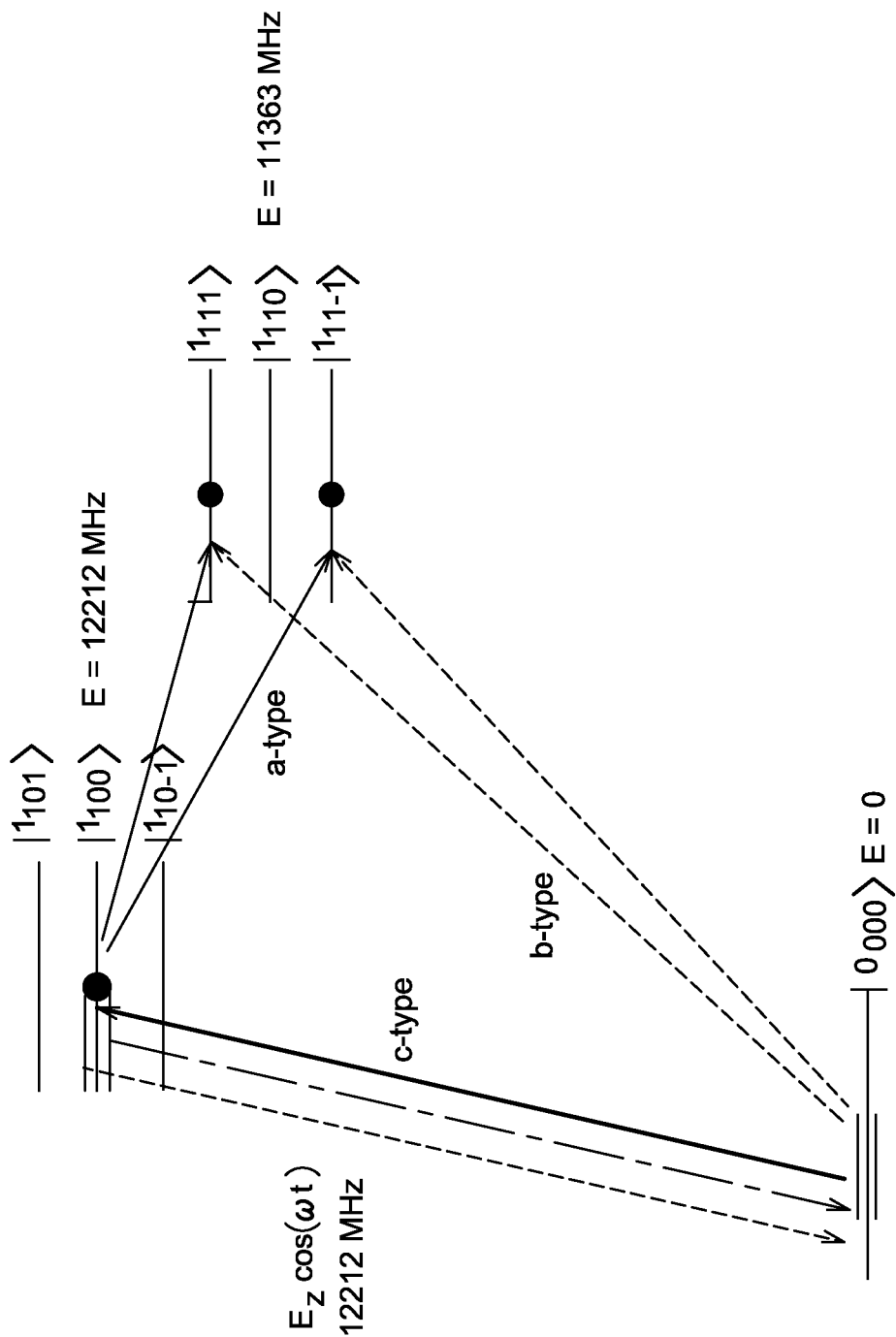
FIG. 5: A: Relevant level structure of 1,2-propanediol. Each state is designated with $|J_{k-1k1m}\rangle$. B: A simulation of 1,2-propanediol in an applied electric field. Applied fields $E_z$ (microwave) and $E_x$ are shown. Also shown is the simulated molecular y polarization for each enantiomer, induced by the change in the time-varying electric field $E_x$. To within experimental uncertainty, the sequence of applied fields shown in this figure corresponds to the fields used to produce the enantiomer-dependent signals in the example of this disclosure.
Figure 5B:
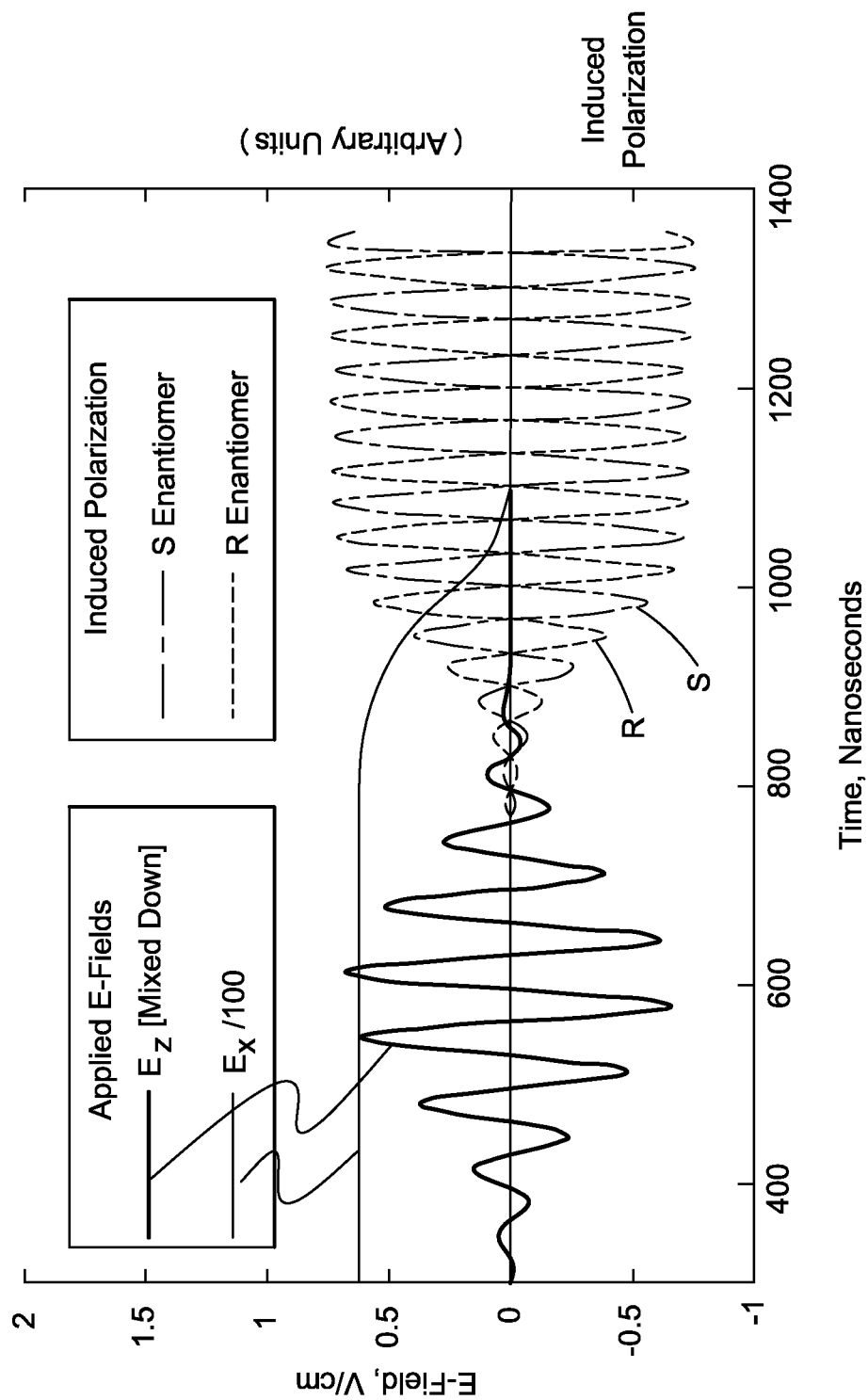

FIG. 5A shows the level structure relevant to another embodiment of this disclosure, using 1-2 propanediol as an example species, and FIG. 5B shows results of simulations for enantiomer-specific detection of 1-2 propanediol. Referring to FIG. 5A, molecules initially in a ground state are prepared in a superposition of $|0_{000}\rangle$ and $|1_{100}\rangle$ via a c-type microwave transition. A change in an electric field $E_x$ mixes in components of $|1_{111}\rangle$ and $|1_{111\text{-}1}\rangle$ with complex phases proportional to $\mu_a$. Allowed electric dipole radiation between these admixed states and the ground state produces an oscillating electric field in the y direction via a b-type transition. This electric field $\in_y$ is proportional to $\mu_a\mu_b\mu_c$ and, therefore, changes sign with enantiomer. Admixing with the $|1_{01}\rangle$ state at about 6,431 MHz (not shown) also contributes a small amount to the chiral signature.

Applied fields $E_z$ (microwave) and $E_x$ are shown in FIG. 5B. The frequency of $E_z$ is about 12,212 MHz, corresponding to the $|0_{00}\rangle \Rightarrow |1_{10}\rangle$ c-type transition. In FIG. 5B, this field is mixed down to about 30 MHz for clarity. Also shown is the simulated molecular y polarization for each enantiomer, induced by the change in the time-varying electric field $E_x$. The induced y polarization is also shown mixed down to about 30 MHz for clarity. The enantiomer-dependent phase of the induced y polarization is evident.

In some implementations, an electric field $E_x$ is switched on before a polarization pulse $P_1$, the polarization pulse $P_1$ is applied, and the electric field $E_x$ is then switched off between the polarization pulse $P_1$ and the detection period. An example timing sequence for such an implementation is shown in FIG. 5B.

In some implementations, the volume 104 is at least partially defined or contained within a microwave cavity formed by a set of cavity mirrors or reflectors 116 and 118 as shown in FIG. 1. In such implementations, the cavity can be tuned such that the resonant frequency $v_{fg}$ of the molecules corresponds to or lies within a transmission mode of the cavity. The cavity can support two modes with substantially identical spatial wave functions and substantially orthogonal polarizations at the frequency $v_{fg}$. In some implementations, the cavity can be a Fabry-Perot type cavity excited in a $T_{00}$ mode. In some implementations, either, or both, of the cavity mirrors 116 and 118 can be translated or tilted to tune the cavity to a desired resonance. A set of electrodes can be included to increase a spatial uniformity of the switched electric field $E_x$ within the cavity.

Figure 6:
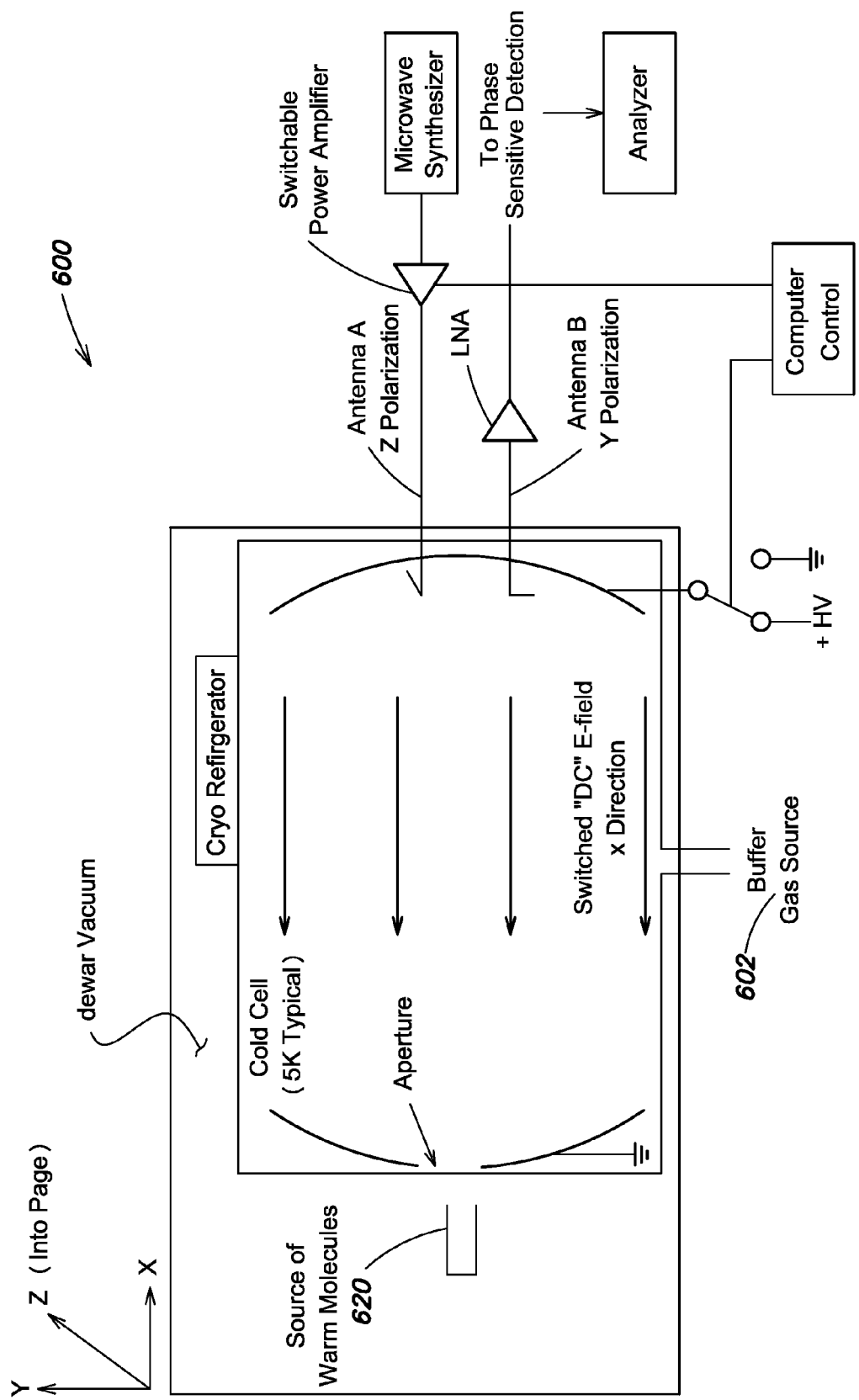
FIG. 6: A spectrometer enhanced to provide enantiomer-specific detection and incorporating a cryogenic buffer gas source to introduce a cold buffer gas.

As explained above, a volume (into which an analyte gas is introduced) can be implemented as a buffer gas cell held at or around cryogenic temperatures. FIG. 6 shows an apparatus 600 incorporating a cryogenic buffer gas source 602, according to another embodiment of this disclosure. Like the apparatus 100 of FIG. 1, the apparatus 600 is configured as a FTMW spectrometer, and defines a volume into which an analyte can be introduced from an analyte source 620. Certain operational aspects and components of the apparatus 600 can be similarly implemented as explained for the apparatus 100 of FIG. 1, and further details regarding those aspects and components are not repeated below.

Referring to FIG. 6, the apparatus 600 is configured to mix a higher temperature analyte gas into a lower temperature buffer gas, thereby forming a supersaturated mixture for spectroscopic analysis. In some implementations, the higher temperature analyte gas is propelled at a first temperature towards the volume in which the analyte gas is to be mixed with the buffer gas. The buffer gas is propelled at a second temperature towards the volume, with the second temperature being lower than the first temperature. In such manner, efficient cooling of the analyte gas can be achieved to result in simplification of a resulting spectrum and improved sensitivity for enantiomer-specific detection of chiral species in the analyte gas.

Figure 7:
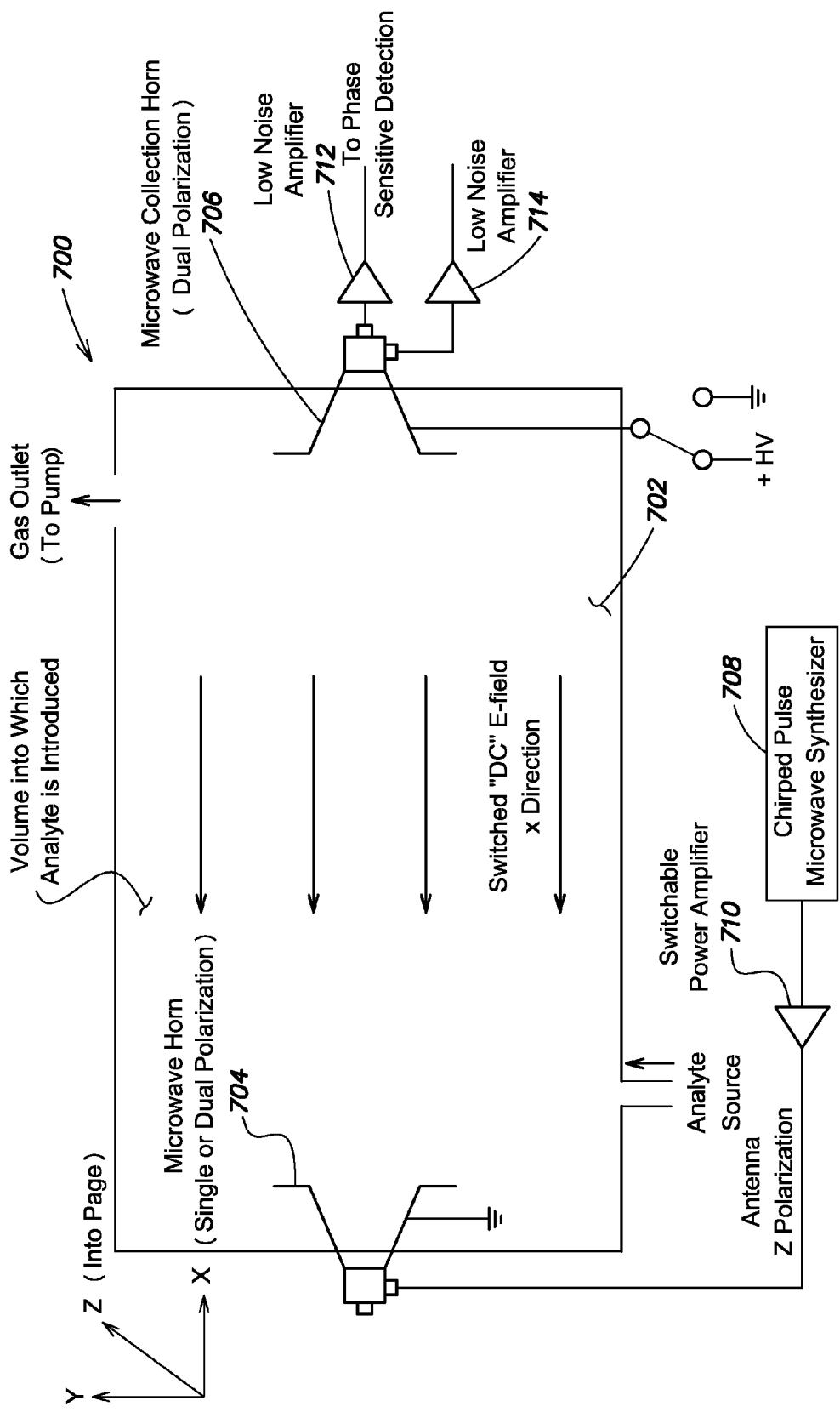
FIG. 7: A chirped-pulse Balle-Flygare type spectrometer enhanced to provide enantiomer-specific detection.

Embodiments of this disclosure also can be implemented to extend the techniques of chirped-pulse FTMW spectroscopy to realize a broadband, enantiomer-sensitive chemical analyzer to detect and quantify specific enantiomers of multiple mixture components substantially simultaneously. FIG. 7 shows an apparatus 700 to perform chirped-pulse FTMW spectroscopy, according to another embodiment of this disclosure. Certain operational aspects and components of the apparatus 700 can be similarly implemented as explained for the apparatuses 100 and 600 of FIGS. 1 and 6, and further details regarding those aspects and components are not repeated below.

Referring to FIG. 7, chirped-pulse FTMW spectroscopy can incorporate high-bandwidth synthesizers and digitizers to excite and record wide bands of microwave spectra of mixtures. To implement this technique in the apparatus 700, the pulse $P_1$ is a broadband chirped pulse with duration less than $\tau_{decoh}$ and an approximately flat spectral density between two frequencies $v_1$ and $v_2$, with at least one frequency $v_{fg}$ of at least one possible analyte component such that $v_1 < v_{fg} < v_2$. Modifications of the apparatus 700 relative to the apparatus 100 of FIG. 1 include a broadband, single or dual polarization input horn 704, a broadband, dual polarization output horn 706, and a microwave generator to produce the chirped pulse through the input horn 704, including a chirped-pulse microwave synthesizer 708 and a switchable power amplifier 710. The output horn 706 collects broadband emitted radiation along a pair of polarization directions. Emitted radiation along one polarization direction (e.g., y-polarized) is conveyed through a LNA 712 for phase-sensitive detection, and emitted radiation along another polarization direction (e.g., z-polarized) is conveyed through a LNA 714 for "traditional" FTMW identification. Although a volume 702 lacks a cavity as shown in FIG. 6, a broadband cavity with relatively low finesse can be included in other implementations.

Figure 8:
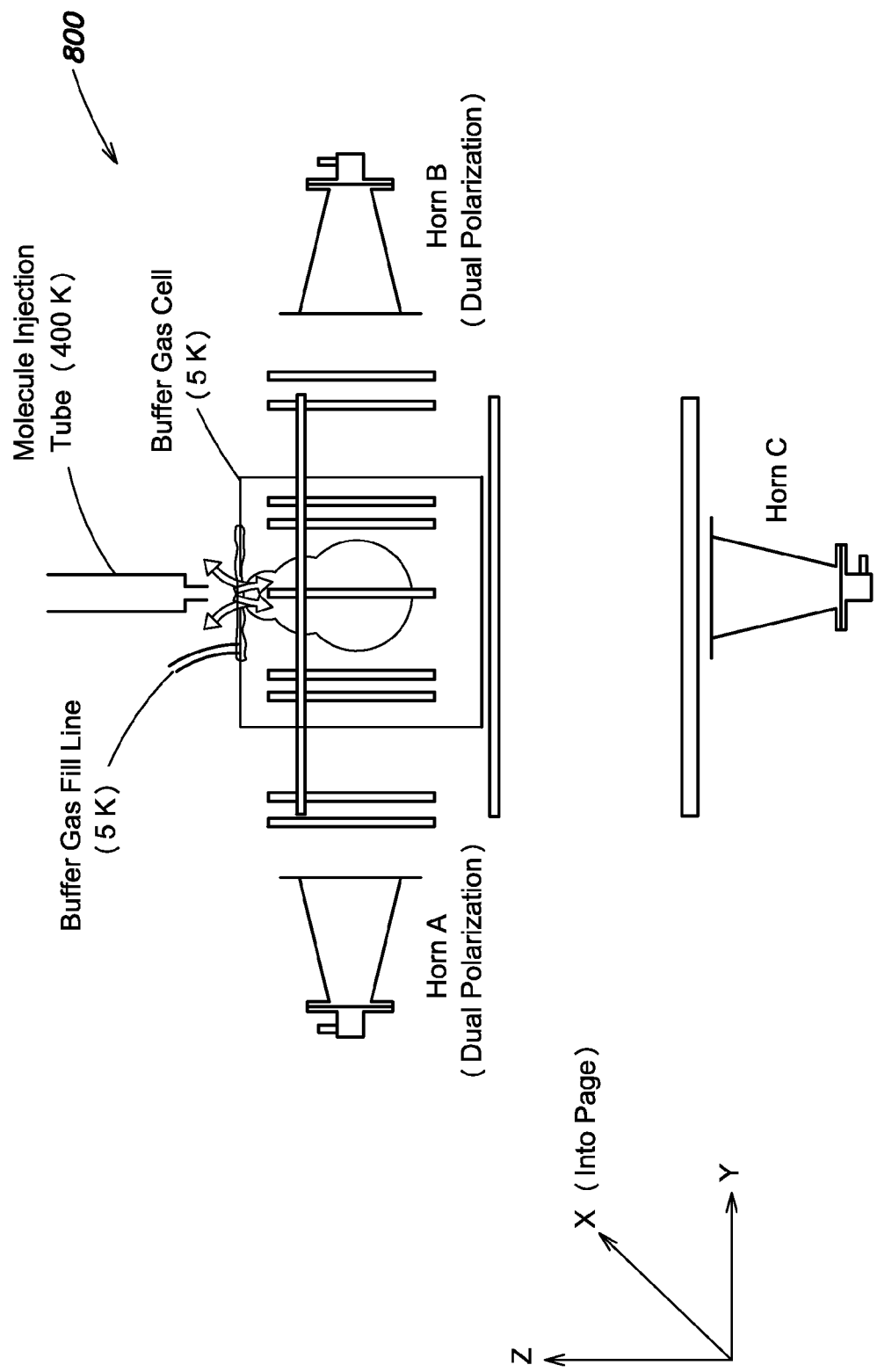
FIG. 8: A cryogenic buffer gas FTMW spectrometer enhanced to provide enantiomer-specific detection.

Embodiments of this disclosure also can be implemented to perform an extension of FTMW spectroscopy referred as enantiomer-dependent, two-color FTMW spectroscopy. FIG. 8 shows an apparatus 800 to perform such an extension of FTMW spectroscopy. Certain operational aspects and components of the apparatus 800 can be similarly implemented as explained for the apparatuses 100, 600, and 700 of FIGS. 1, 6, and 7, and further details regarding those aspects and components are not repeated below.

Referring to FIG. 8, vertical lines show wavefronts for a microwave pulse $P_1$ that is linearly polarized substantially along the z direction and wavefronts for another microwave pulse $P_2$ that is linearly polarized substantially along the x direction. The pulses $P_1$ and $P_2$ can be applied in any order or substantially simultaneously. A collected pulse $P_3$ is linearly polarized substantially along the y direction, and radiates downwardly. Horn A transmits the pulses $P_1$ and $P_2$ in substantially orthogonal polarizations, and horn B collects "traditional" FTMW radiation in different polarizations. Horn C collects the induced radiation that is substantially orthogonal to both $P_1$ and $P_2$.

In effect, microwave pulses $P_1$ and $P_2$ with substantially orthogonal polarizations can be used on a-type and b-type transitions respectively to prepare a molecule in a superposition, which includes levels connected via a c-type transition. The electric field of the radiation emitted on that transition is proportional to $\mu_a\mu_b\mu_c$, and hence shows about ±180° phase shift between enantiomers. In a racemic mixture, the radiation from opposite enantiomers can substantially cancel, and little or no radiation can be emitted from the c-type transition.

Figure 9:
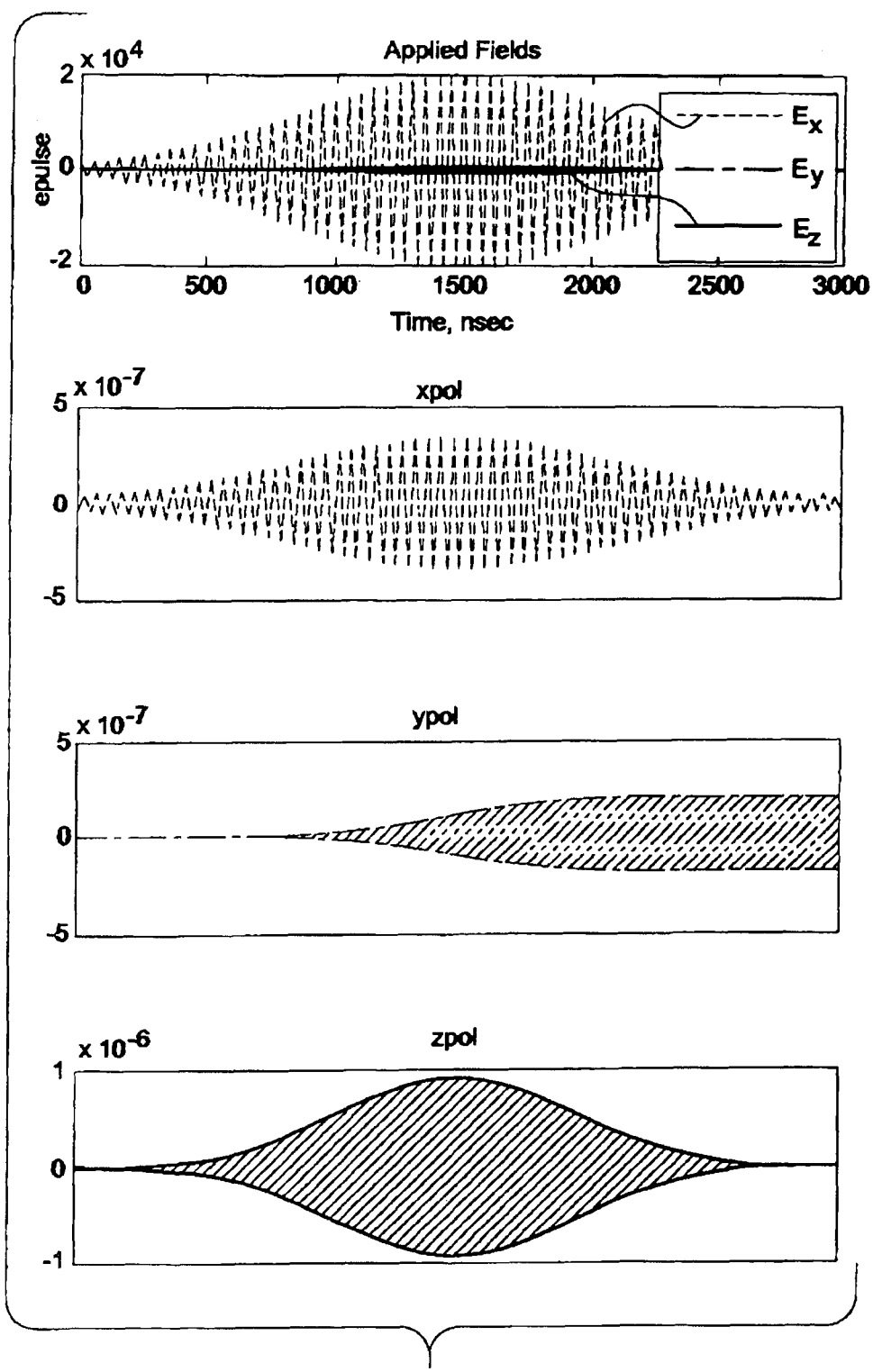
FIG. 9: A pulse sequence including a lower frequency pulse at about 20 MHz and a higher frequency pulse that is de-tuned from resonance by about 20 MHz. An enantiomer-dependent polarization is induced along the y direction, and is enhanced by more than a factor of about 10 compared to the sequence described in FIG. 4. In addition, the z-polarized, "traditional" signal is highly suppressed at the end of the pulse sequence. This suppression serves to reduce unwanted crosstalk between the z-polarized radiation and an antenna oriented to collect primarily or solely y-polarized radiation. Also, emitted radiation is at a frequency distinct from any applied frequency. The applied field $E_z$ of about 5 V/cm is not readily visible on the scale of the plot in the upper left of FIG. 9.
Figure 9:
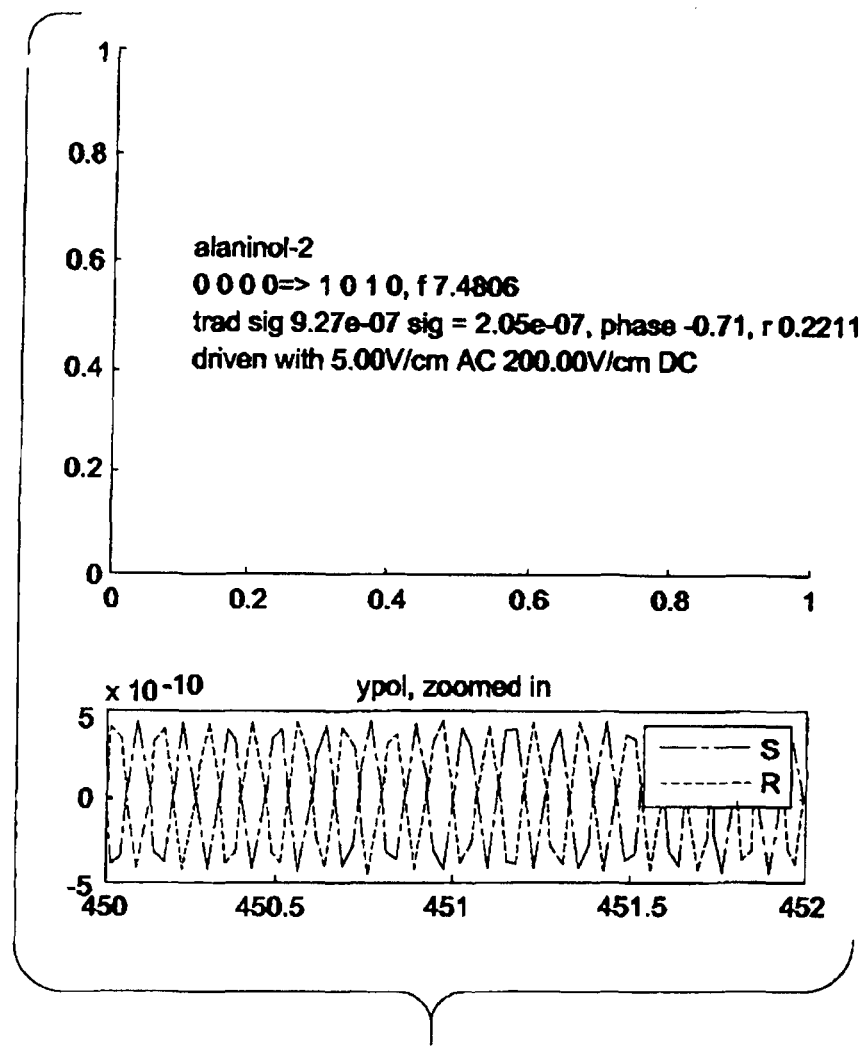

In the case of detuned, two-color FTMW spectroscopy, pulse sequences can be optimized to yield stronger enantiomer-dependent signals. An example of such a pulse sequence is shown in FIG. 9. In this pulse sequence, two Gaussian pulses $P_1$ and $P_2$ are applied: one with x polarization at a lower frequency $v_1$ (about 20 MHz in FIG. 9), and one with z polarization at a higher frequency $v_2=v_{trans}-v_1$, where $v_{trans}$ is the frequency of an allowed microwave transition in a molecule being analyzed. The amplitude of the higher frequency pulse $P_2$ is tuned such that it induces Rabi oscillations at or below a frequency of $v_1/2$; that is, within each oscillation of an applied field along the x direction, molecules undergo a $\pi/2$ rotation or less. This pulse sequence can dramatically increase the amplitude of an enantiomer-dependent induced polarization along the y direction, as evident from simulation results for the chiral molecule alaninol shown in FIG. 9. As an additional benefit, this pulse sequence can suppress a non-enantiomer-dependent polarization along the z direction. Large amplitude oscillations in z-oriented polarization sometimes can lead to systematic offsets due to coupling between orthogonally polarized cavity modes.

A suitable cavity for the pulse sequence shown in FIG. 9 can have two high quality factor modes with substantially similar spatial modes, substantially orthogonal polarization, and slightly different (e.g., different by about $v_1$) resonant frequencies. Such a cavity can be implemented such that both the z-polarized pulse at $v_2$ and the induced y-oriented polarization at $v_{trans}$ are resonantly enhanced by the cavity. Such a cavity can be implemented by placing grooves or slits of a specified orientation and a specified depth in one or both of a pair of mirrors. Alternatively, or in conjunction, such a cavity can be implemented by weakly coupling another microwave element, such as a waveguide stub, to a main cavity in a polarization-dependent manner. The resulting cavity can have a number of other desirable properties, such as essentially zero crosstalk between orthogonal polarizations and separate addressing of orthogonal modes.

In the case of double resonance, two-color FTMW spectroscopy, both pulses—one with z polarization and one with x polarization—can be targeted at resonances of molecules, thereby allowing a-type, b-type, and c-type transitions to be addressed directly. The x-polarized pulse can correspond to an axial radio frequency (RF) field of lower frequency compared to the z-polarized pulse. In some implementations, the applied axial field is of a low enough frequency that a substantially spatially uniform field is applied to an entire sample. For example, a 15 cm cell can be subjected to an axial field at a frequency of no greater than about 1,000 MHz.

Figure 10:
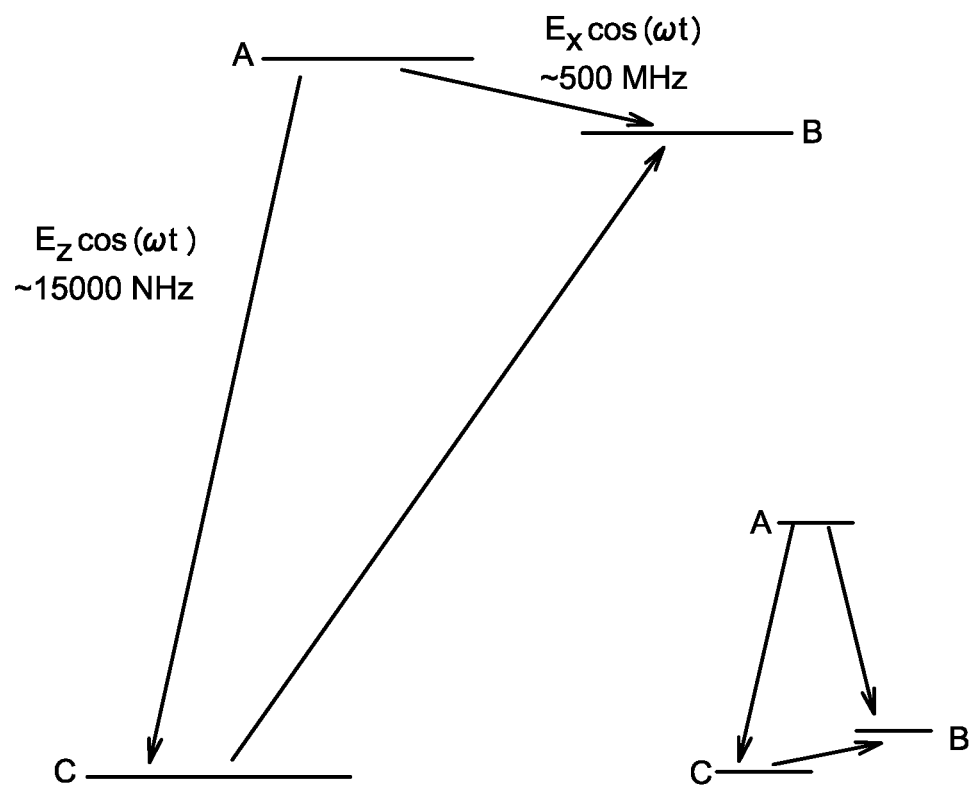
FIG. 10: Level structure for a double resonance chirality determination. Levels A and C are mixed via a microwave pulse; either subsequently or simultaneously, levels A and B are mixed via a radio frequency pulse. Microwaves at the B ⇒ C transition are emitted. The smaller inset is another suitable level structure. A spectrometer is sized to be small enough that a substantially spatially uniform field can be applied corresponding to the A ⇒ B transition; for a cutoff of about 1,000 MHz, this size can be about λ/2 or about 15 cm.

FIG. 10 shows a level structure of a molecule that can be subjected to double resonance, two-color FTMW spectroscopy. Three rotational levels, referred as A, B, and C, are involved. The notation $v_{AB}$ denotes a frequency of the A⇒B transition, or formally $(E_A-E_B)/h$. It can be observed from FIG. 10 that $v_{AC}=v_{AB}+v_{BC}$. Here, A, B, and C are chosen such that $E_A>E_B>E_C$; that is, the levels are listed in descending order.

More specifically, the levels A, B, and C can conform to the following conditions:
(1) Each of the A⇒B, B⇒C, and A⇒C transitions corresponds to an allowed electric dipole transition.
(2) One of $v_{AB}$ or $v_{BC}$ is between a few MHz and a frequency $v_{cutoff}$. $v_{cutoff}$ is chosen such that a wavelength $c/v_{cutoff}>2L$, where L is a size of an active region of a spectrometer. For example, if L is about 15 cm, $v_{cutoff}$ can be about 1,000 MHz.
(3) The other two transitions are of appropriate frequencies to be driven and detected by the spectrometer. One of these transitions is desirably strong, as a final signal strength can be proportional to this transition strength.

A molecule with a suitable triad of levels A, B, and C can exhibit:
(1) A strong transition between about 3 GHz and about 18 GHz, with a strength within a factor of about 4 of the strongest transition in the molecule.
(2) A reasonably strong transition between about 5 MHz and about 400 MHz.
(3) Projected microwave and RF powers less than about 10 Watts for suitable experimental conditions.

In a given triad, the low frequency transition and one of the high frequency transitions are subject to drive pulses, while induced radiation on the other high frequency transition is monitored. In some cases, as shown in FIG. 10, this results in induced radiation at the sum frequency, $v_3=v_1+v_2$. In other cases, the induced radiation is at the difference frequency, $v_3=v_1 v_2$. In some embodiments, it is advantageous to choose one or the other of these schemes based on the strength of the transitions, with the monitored transition at $v_3$ corresponding to the strongest line. In the examples below, "drive" refers to the weaker of the two high frequency transitions, "twist" refers to the low frequency transition, and "listen" refers to the other (stronger) high frequency transition. [about 0.xx of best] indicates the strength of the expected signal compared to the strongest signals that can be expected in traditional FTMW spectroscopy.

The following is a list of examples of suitable triads of levels for a wide range of chiral molecules. In each case, a "drive" transition is one of the higher frequency transitions, and a "twist" transition is the lower frequency transition (<400 MHz).

1-2 Propanediol:
drive |2 1 1>=>|2 2 1> type c at about 14.796 GHz,
twist |2 2 1>=>|2 2 0> type a at about 0.100 GHz,
listen |2 1 1>=>|2 2 0> type b at about 14.896 GHz,
strength of about 3.89e-006 [about 0.64 of best]
Carvone—Equatorial Conformer 2:

Example 1 drive |3 1 2>=>|3 2 2> type c at about 4.630 GHz,
twist |3 2 2>=>|4 1 3> type b at about 0.462 GHz,
listen |3 1 2>=>|4 1 3> type a at about 5.091 GHz,
strength of about 4.14e-006 [about 0.50 of best]

Example 2 drive |6 1 5>=>|6 2 5> type c at about 4.076 GHz,
twist |6 2 5>=>|6 2 4> type a at about 0.186 GHz,
listen |6 1 5>=>|6 2 4> type b at about 4.262 GHz,
strength of about 7.25e-006 [about 0.88 of best]

Example 3 drive |6 2 4>=>|6 3 4> type c at about 7.960 GHz,
twist |6 2 5>=>|6 2 4> type a at about 0.186 GHz,
listen |6 2 5>=>|6 3 4> type b at about 8.146 GHz,
strength of about 6.03e-006 [about 0.73 of best]
Glycidol:

Example 1 drive |1 0 1>=>|1 1 1> type c at about 6.246 GHz,
twist |1 1 1>=>|1 1 0> type a at about 0.320 GHz,
listen |1 0 1>=>|1 1 0> type b at about 6.566 GHz,
strength of about 2.99e-006 [about 0.84 of best]

Example 2 drive |4 1 3>=>|4 2 3> type c at about 17.638 GHz,
twist |4 2 3>=>|4 2 2> type a at about 0.179 GHz,
listen |4 1 3>=>|4 2 2> type b at about 17.817 GHz, strength of about 2.78e-006 [about 0.78 of best]
Alaninol-2:

Example 1 drive |2 1 1>=>|2 2 1> type c at about 6.952 GHz,
twist |2 2 1>=>|2 2 0> type a at about 0.177 GHz,
listen |2 1 1>=>|2 2 0> type b at about 7.129 GHz, strength of about 2.93e-006 [about 0.32 of best]

Example 2 drive |4 2 3>=>|4 3 1> type c at about 14.309 GHz,
twist |4 3 2>=>|4 3 1> type a at about 0.170 GHz,
listen |4 2 3>=>|4 3 2> type b at about 14.139 GHz, strength of about 2.94e-006 [about 0.32 of best]
1,2 Butanediol:
drive |4 1 4>=>|4 2 2> type c at about 16.319 GHz,
twist β 2 1>=>|4 1 4> type b at about 0.290 GHz,
listen β 2 1>=>|4 2 2> type a at about 16.609 GHz, strength of about 4.07e-006 [about 0.49 of best]

Figure 11:
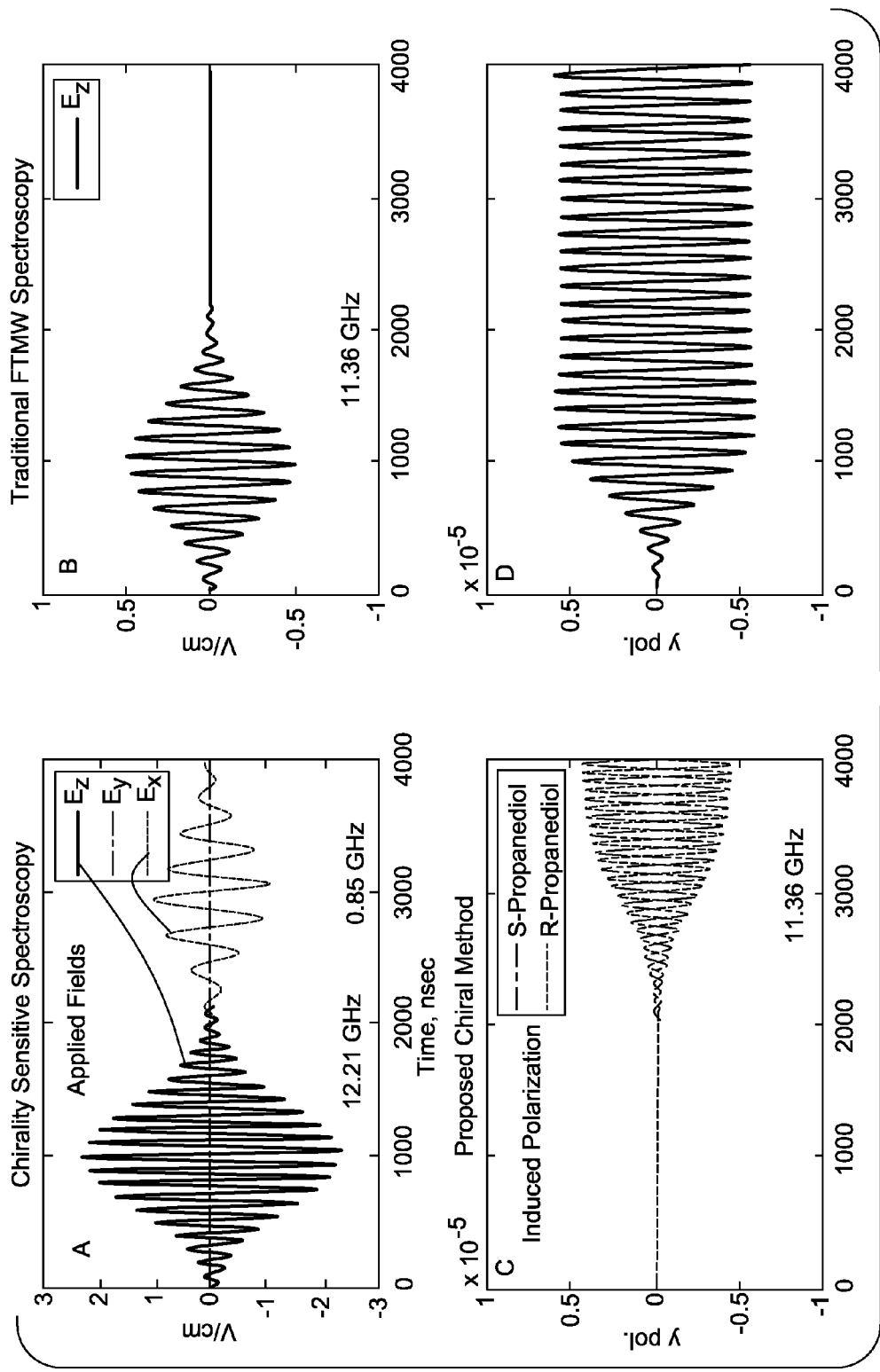
FIG. 11: Simulations of a double resonance chirality determination. Here, an applied radio frequency field is about 854 MHz. A: Applied fields. All fields shown are mixed down for ease of illustration, with actual frequencies labeled. The y axis is in absolute V/cm. B,D: Applied fields and induced signal for a "traditional" FTMW experiment on a 11,363 MHz line. C: Induced, chirality-dependent signal, which radiates at about 11,363 MHz. In both A and B, applied fields have been chosen to optimize signal strength.

FIG. 11 shows a timing simulation for double resonance, two-color FTMW spectroscopy. As shown in the upper panel of FIG. 11, the z-polarized pulse and the x-polarized pulse are sequentially applied, although the pulses also can be applied substantially simultaneously. Also, amplitudes of both pulses can be substantially reduced.

Figure 12:
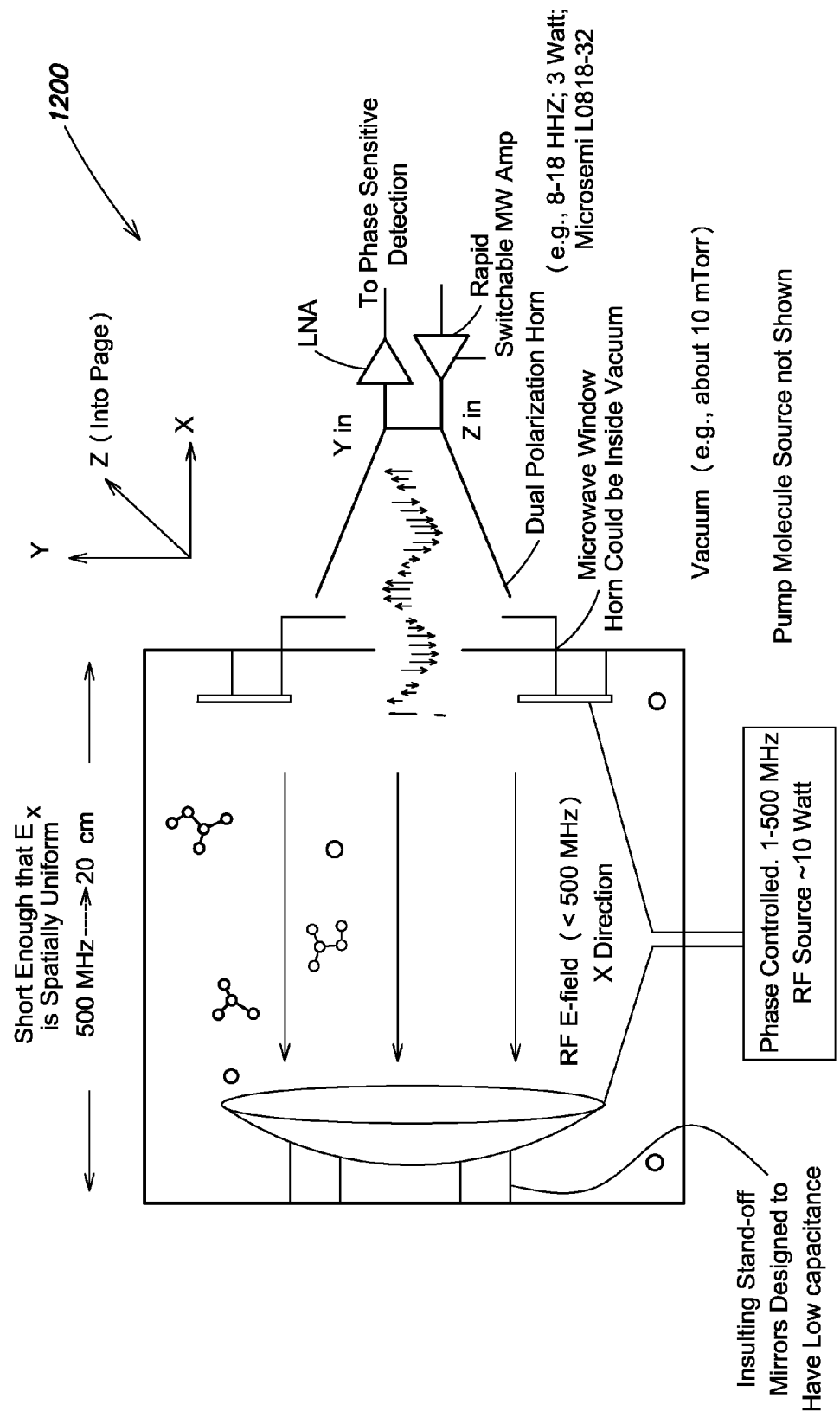
FIG. 12: A spectrometer enhanced to provide enantiomer-specific detection via a double resonance chirality determination.
Figure 13:
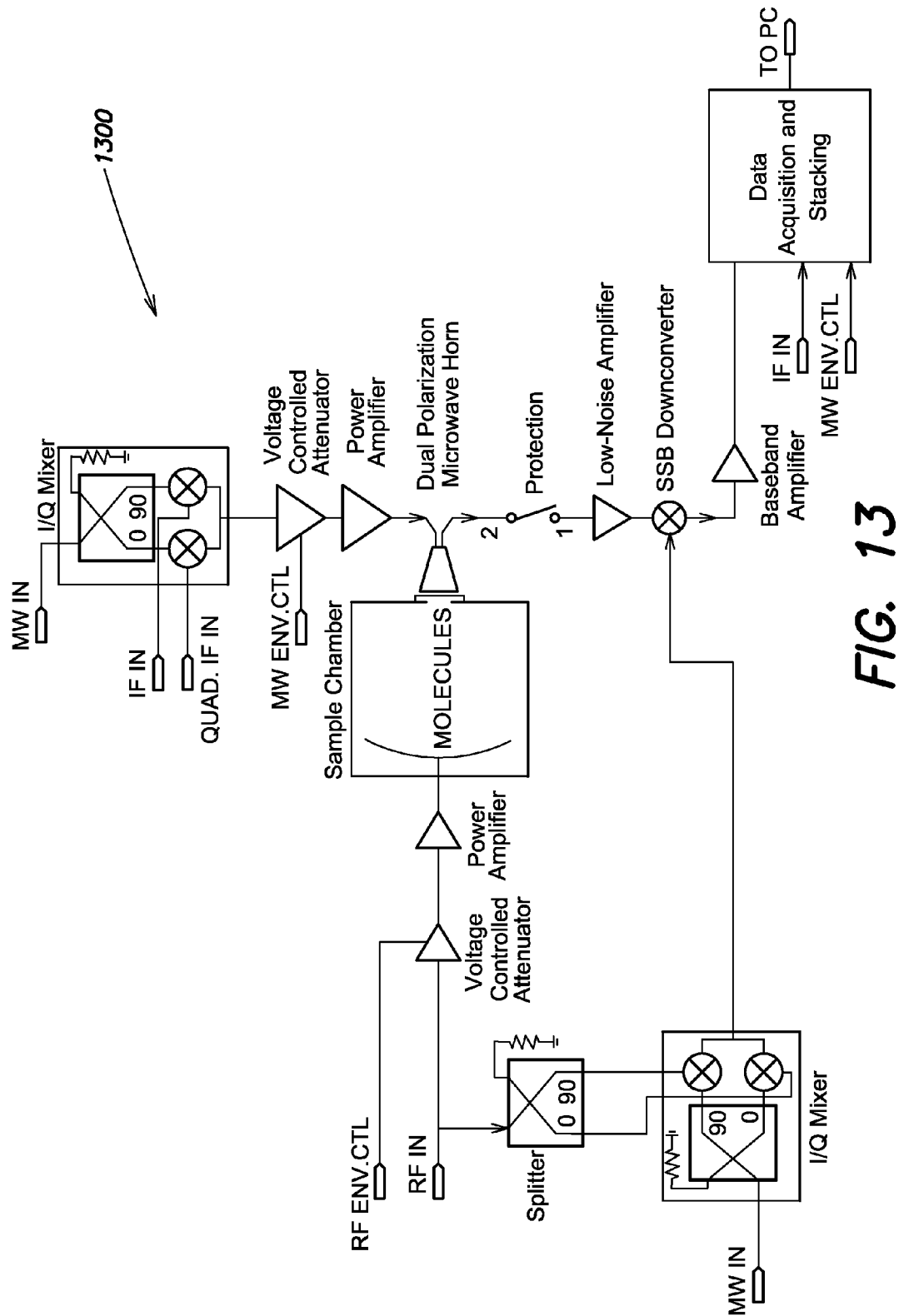
FIG. 13: A drive circuit for the spectrometer of FIG. 12. Microwave and radio frequency inputs (labeled as MW IN and RF IN) can run continuously (in this example at about 14.980 GHz and about 400 MHz, respectively). Intermediate signals, such as a microwave drive signal at about 15.000 GHz and a detection local oscillator signal at about 15.380 GHz, are derived from these inputs. A third input (labeled as IF IN) can run continuously at about 20 MHz, although this input also be generated in a phase controlled manner or can be gated to reduce crosstalk.

FIG. 12 shows an apparatus 1200 to perform double resonance, two-color FTMW spectroscopy, and FIG. 13 shows a drive circuit 1300 for the apparatus 1200. Certain operational aspects and components of the apparatus 1200 can be similarly implemented as explained for the apparatuses 100, 600, 700, and 800 of FIGS. 1, 6, 7, and 8, and further details regarding those aspects and components are not repeated below.

As shown in FIG. 12, a cavity is omitted from the apparatus 1200, thereby allowing simplification of its design and the omission of moving and precision machined components. Microwaves are introduced and detected in two polarizations via a dual polarization horn, although two horns can be included in other implementations. The microwaves cross a chamber and are reflected back into the horn via a spherical mirror. The microwaves pass through an annular electrode. The electrode and the spherical mirror can be subjected to a high frequency RF field. A capacitance of the mirror can be set to be low, such as about 10 pF as a borderline capacitance (Z of about 30 Ohms). The phase of both RF and microwave inputs can be suitably controlled.

The apparatus 1200 affords a number of advantages, including:

(1) High strength signals that are within a factor of about 2 of the strongest lines in "traditional," non-chiral FTMW spectroscopy.
(2) Omission of high voltage components, resulting in cost savings, improved reliability, and avoiding issues with discharges.
(3) High specificity associated with a double resonance experiment;
(4) Modest power levels are sufficient, even for larger systems.

Conversely, if either, or both, high RF and microwave powers are available, signals from candidates with at least one of $\mu_a$, $\mu_b$, and $\mu_c$, close to zero can be resolved. The signal-to-noise ratio from these candidates can be set by their highest dipole moment component, while the energy budget is approximately set by the lowest component. A small dipole moment component specifies a larger driving field, and a short decoherence time also specifies a larger driving field. For example, about 40 Watts RF or microwave can be sufficient drive transitions for molecules with $\mu_a$, $\mu_b$, or $\mu_c$ of about 0.1 Debye and a coherence time of about 1 μs.

(5) Parallelizable to allow simultaneous application of multiple pairs of RF and microwave pulses.

Figure 14:
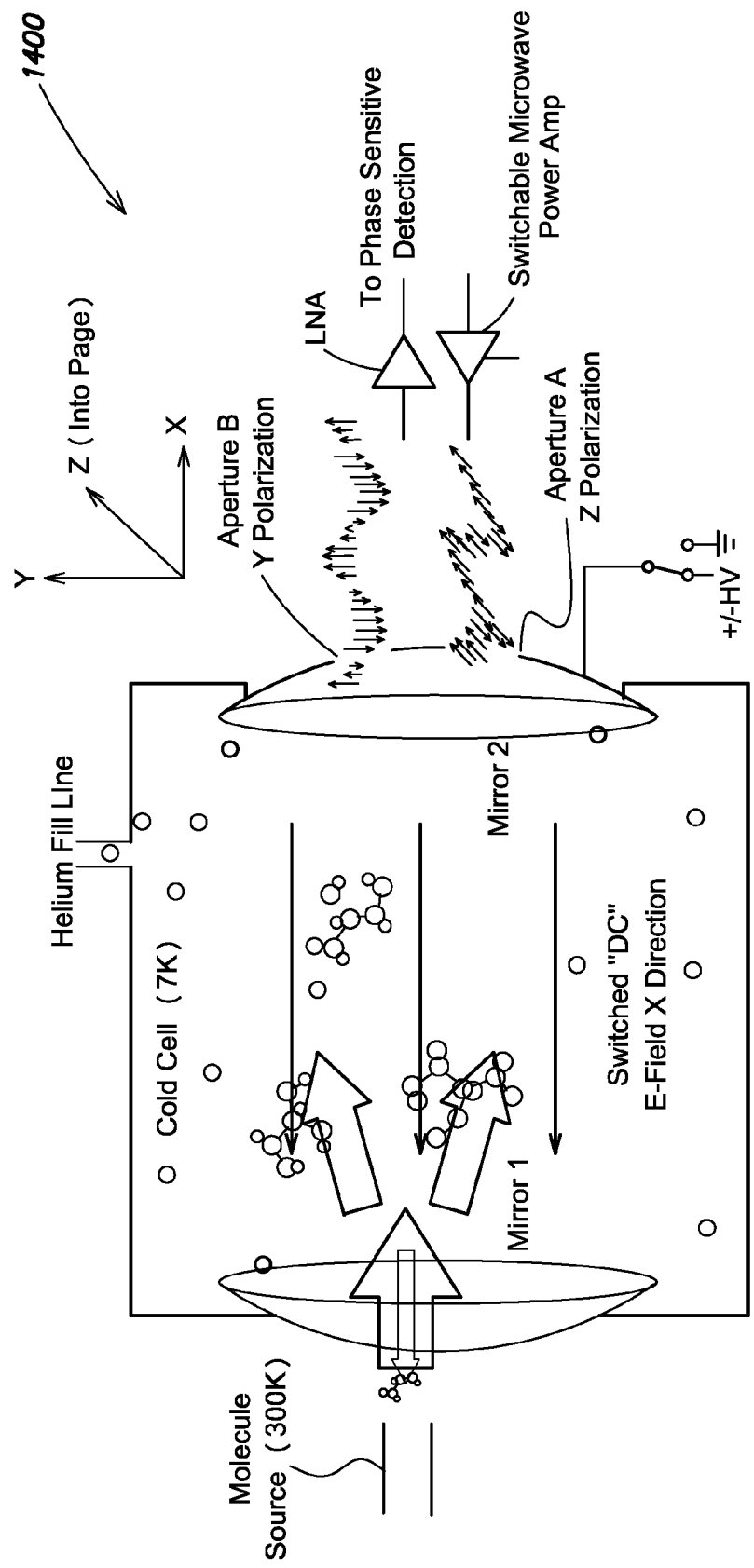
FIG. 14: A spectrometer enhanced to provide enantiomer-specific detection and to couple into a cavity via apertures.

Embodiments of this disclosure also can be implemented to provide coupling to cavity modes of substantially orthogonal polarization via apertures or arrays of slits. FIG. 14 shows an apparatus 1400 to perform FTMW spectroscopy, according to another embodiment of this disclosure. Certain operational aspects and components of the apparatus 1400 can be similarly implemented as explained for the apparatuses 100, 600, 700, 800, and 1200 of FIGS. 1, 6, 7, 8, and 12, and further details regarding those aspects and components are not repeated below.

Referring to FIG. 14, a cavity supports modes of substantially orthogonal polarization, and these modes can be separately addressed via waveguides coupled to a mirror (denoted as mirror 2 in FIG. 14) and coupled into the cavity via apertures formed in the mirror (denoted as A and B in FIG. 14). Such manner of coupling into the cavity can provide desired isolation between orthogonal modes, without undue perturbation of the cavity. When operating at lower frequencies, such as below about 60 GHz or from about 12 GHz to about 18 GHz, either, or both, of the waveguides can be replaced with coaxial cables. At higher frequencies, waveguides can be more desirable for certain implementations.

An additional modification of the apparatus 1400 is directed to a technique to reduce systematic errors via reversals of an applied electric field. An enantiomer-dependant signal $\in_y$ changes sign when the sign of an applied electric field $E_x$ is reversed. Many systematic errors, such as phase shifts from non-uniform fields and crosstalk between nominally orthogonal channels, are substantially identical for opposite signs of $E_x$. The reversal in $\in_y$ can be exploited by subtracting traces taken with substantially equal and opposite signs of the applied field $E_x$, thereby cancelling the systematic errors while doubling the enantiomer-dependent signal.

In the embodiment of FIG. 14, cancelling of systematic errors can proceed as follows. For a given, positive value of a voltage $V_x$ applied to the mirror, the induced signal $\in_y$ is measured under conditions where a polarization pulse $P_1$ is applied with $V_{mirror}=V_x$, and then changed to $V_{mirror}=0$ at some time t during the resulting free induction decay. This measured signal can be denoted as $\in_1(t)$. Next, $\in_2(t)$ is measured under conditions where the polarization pulse $P_1$ is applied with $V_{mirror}=-V_x$, and then changed to $V_{mirror}=0$ at the same time t. Next, the phase of a difference signal $\in_{diff}=\in_1(t)-\in_2(t)$ is computed. The phase of $\in_{diff}(t)$ changes with enantiomer and is less susceptible to systematic errors than either $\in_1(t)$ or $\in_2(t)$ alone. This phase measurement can be a differential measurement, namely the phase is measured by comparing to a reference phase, such as the phase of $P_1$.

Figure 15:
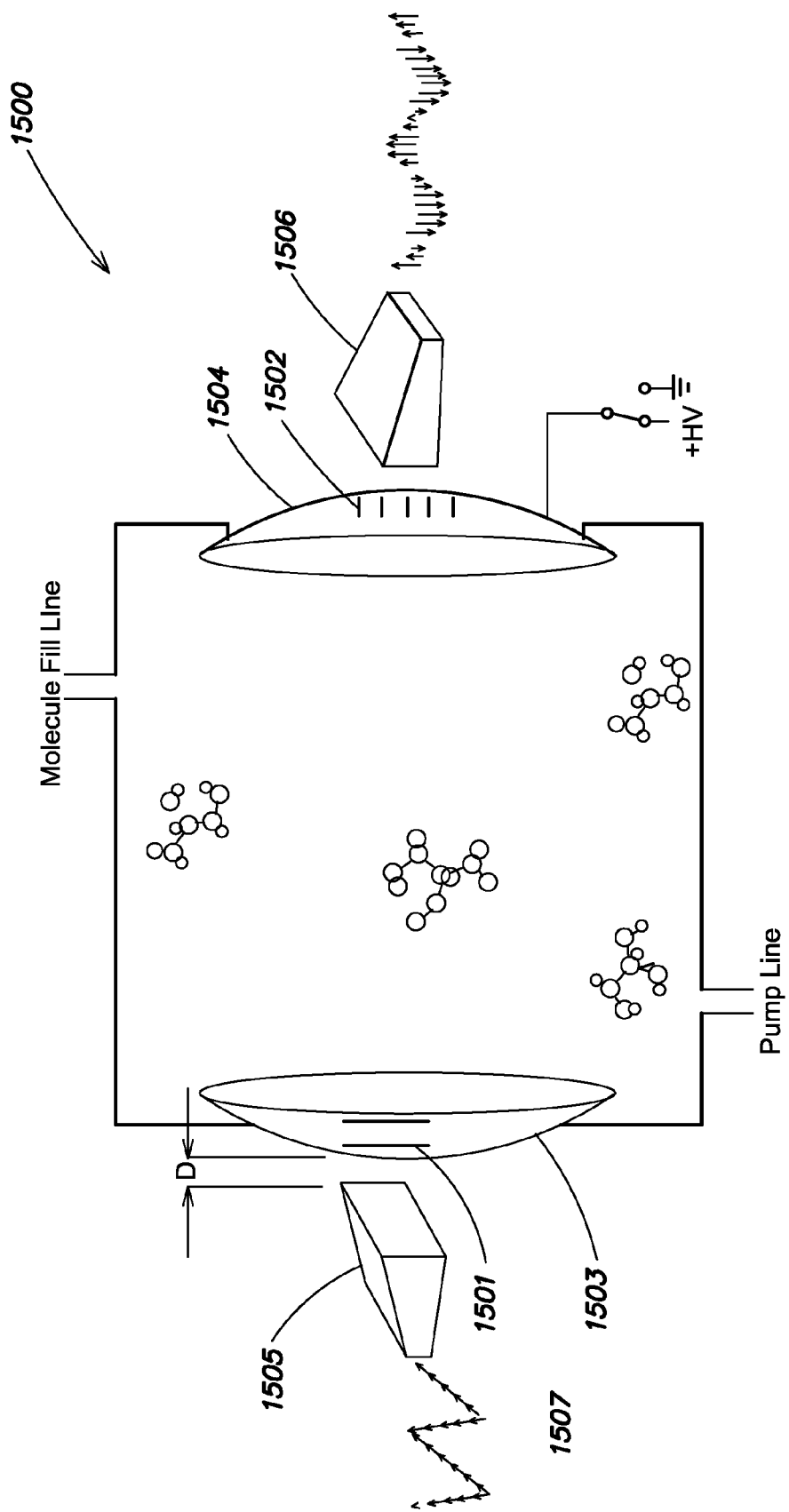
FIG. 15: A spectrometer enhanced to provide enantiomer-specific detection and to couple into a cavity via arrays of slits.

FIG. 15 shows an apparatus 1500 to perform FTMW spectroscopy, according to another embodiment of this disclosure. Certain operational aspects and components of the apparatus 1500 can be similarly implemented as explained for the apparatuses 100, 600, 700, 800, 1200, and 1400 of FIGS. 1, 6, 7, 8, 12, and 14, and further details regarding those aspects and components are not repeated below.

Referring to FIG. 15, a pair of polarization-dependent mirrors 1503 and 1504 in the microwave regime are implemented such that an array of relatively long, thin slits are formed in a central portion of each of the pair of mirrors 1503 and 1504. Microwaves polarized substantially parallel to the slits are reflected, while microwaves polarized substantially perpendicular to the slits are slightly transmitted. Coupling of cavity modes is carried out via the arrays of slits (denoted as 1501 and 1502 in FIG. 11). The slits in one mirror are oriented substantially orthogonally to the slits in the other. A microwave horn 1505 or 1506 is coupled behind each of the arrays of slits 1501 and 1502. The horns 1505 and 1506 are oriented to collect and emit radiation of an appropriate polarization that passes through the slits, namely with the polarization substantially orthogonal to the long axis of the slits. The thickness, length, and width of the slits specify a quality factor Q of each orthogonally polarized mode. In typical operation, $Q_z$ and $Q_y$ can be set to be substantially equal, although $Q_z$ and $Q_y$ also can be set to be different. Both cavity modes can be critically coupled or over-coupled. Specifically, the dominant loss mechanism for z-polarized radiation in the cavity can be via the array of y-oriented slits in the mirror 1503, and the dominant loss mechanism for y-polarized radiation in the cavity can be via the array of z-oriented slits in the mirror 1504. The extent of the arrays of slits 1501 and 1502 is about the same size as the $T_{00}$ mode of the cavity, and an output aperture of the horns 1505 and 1506, in turn, is set to be about the same size as the arrays of slits 1501 and 1502. This matching of sizes allows for mode matching between a spatial mode of the cavity and an output mode of the horns 1505 and 1506. By operating in such manner, radiation in each of the orthogonally polarized modes can be critically coupled to a respective one of a pair of coupled waveguides or coaxial cables.

Although most microwaves that are transmitted through the slits can be collected by the horns 1505 and 1506, a fraction of the microwaves can be reflected back towards the mirrors 1503 and 1504. In turn, a fraction of these reflected microwaves can be re-transmitted into the cavity. This reflected fraction can be enhanced, such as by placing sheets of a dielectric material (such as denoted by 1507 in FIG. 15) between the mirrors 1503 and 1504 and the horns 1505 and 1506. Because microwaves reflected from the horns 1505 and 1506 or from the dielectric sheets re-enter the cavity with a phase shift that depends on the geometry of the horns 1505 and 1506 and the dielectric sheets, tuning of this geometry, such as by adjustment of a gap D between the back of the mirror 1503 and the horn 1505, can result in polarization-dependent tuning By operating in such manner, separate tuning of the frequency and quality factor Q of orthogonally polarized modes can be achieved. Such a cavity can represent a tunable implementation of a cavity for two-color, enantiomer-dependent spectroscopy.

In the case of cavity-enhanced, enantiomer-specific spectroscopy, both the strength of a polarization pulse and a resulting signal can be enhanced by a high quality factor Q of a cavity. Q can be specified as a ratio between a frequency of a cavity mode and a linewidth of that mode. Q typically cannot be raised arbitrarily, since a weak microwave signal is typically detected once the cavity has "rung down", which can last for a time period proportional to an inverse of the linewidth. In some embodiments, a cavity can be implemented to allow rapid switching between "high Q" and "low Q". Such a Q-switched cavity can be operated according to the following sequence:

1. Set the cavity for "high Q" and introduce a microwave pulse or a pulse sequence, which can induce an oscillating dipole in a molecular sample.
2. After molecules in the sample are polarized, briefly switch the cavity to "low Q". This switching can efficiently damp microwave pulses that are previously introduced, but with little or no effect on the oscillating molecules.
3. Next, the cavity can be switched back to "high Q", enhancing a detected signal from the oscillating molecules.

Such a Q-switched cavity can provide the benefits of a high Q cavity (e.g., high polarization and high sensitivity), without a dead time typically associated with ringing down of cavities. A Q-switched cavity can be implemented by weakly coupling the cavity to a coaxial cable, such as via an antenna, an aperture, or an array of slits, and coupling the coaxial cable to a rapidly switchable microwave switch, such as a pin diode.

The apparatuses 100, 600, 700, 800, 1200, 1400, and 1500 can be calibrated according to one of at least a pair of calibration techniques. In one technique, calibration is carried out for each enantiomer R-X and S-X by introducing a known amount of pure R-X and S-X into a spectrometer. Signals from an unknown analyte can then be compared to the calibration signals. In another technique, a known amount of one or more pure chiral substances Y are introduced into the spectrometer. The chiral substances Y have sufficiently dense rotational spectra such that a phase-sensitive response of a cavity and microwave components can be mapped out over a substantial fraction of a bandwidth (e.g., substantially the entire bandwidth) of the spectrometer. The enantiomer-dependent response from any species X can then be predicted from this response function and the calculated or known molecular constants of X.

Certain embodiments of this disclosure differ from circular dichroism spectroscopy. Circular dichroism spectroscopy typically depends on interference effects between electric dipole transitions and either magnetic dipole transitions or electric quadrupole transitions. Without these weaker transitions, responses of molecules to left circularly polarized light and right circularly polarized light typically cannot be distinguished. Optical rotation effects, therefore, typically vanish in the long wavelength limit where the wavelength is greater or much greater than the size of the molecules, as is typically the case for the microwave regime. In contrast, the extensions of FTMW spectroscopy in some embodiments can be based primarily or solely on electric dipole transitions. Additionally, the extensions of some embodiments can involve a resonant interaction between microwaves of a pulse $P_1$ and analyte molecules. This resonant interaction is allowed by the relatively long decoherence time in gas phase molecules; in contrast, circular dichroism spectroscopy is typically non-resonant and performed on liquid samples with very short decoherence times.

Although certain embodiments are explained in the foregoing, other embodiments are contemplated and encompassed by this disclosure. For example, in addition to a Balle-Flygare type spectrometer, other types of spectrometers can be enhanced to provide enantiomer-specific detection, such as a coaxially oriented beam-resonator arrangement (COBRA)-type spectrometer or a coaxially aligned electrodes for Stark effect applied in resonators (CAESAR)-type spectrometer. In addition to a FTMW spectrometer, spectrometers also can be configured to perform other types of rotational spectroscopy, such as microwave-microwave double resonance spectroscopy, infrared-microwave double-resonance spectroscopy, or microwave-UV double-resonance spectroscopy. For example, a polarizing microwave pulse in the z direction can be replaced with a z-polarized infrared laser pulse. Enantiomers can be detected via phase-sensitive heterodyne detection of a y-polarized infrared free induction decay. Alternatively, or in conjunction, addition of a second, phase-controlled y-polarized infrared pulse in place of a detection operation can preferentially leave one enantiomer in an excited vibrational state. Molecules in this state subsequently can be photo-dissociated or otherwise selectively addressed via a third light source, resulting in net enantiopurification of an originally racemic sample.

Examples

The following examples describe specific aspects of some embodiments of this disclosure to illustrate and provide a description for those of ordinary skill in the art. The examples should not be construed as limiting this disclosure, as the examples merely provide specific methodology useful in understanding and practicing some embodiments of this disclosure.

Enantiomer-Specific Detection of the Chirality of 1,2-Propanediol

Figure 16:
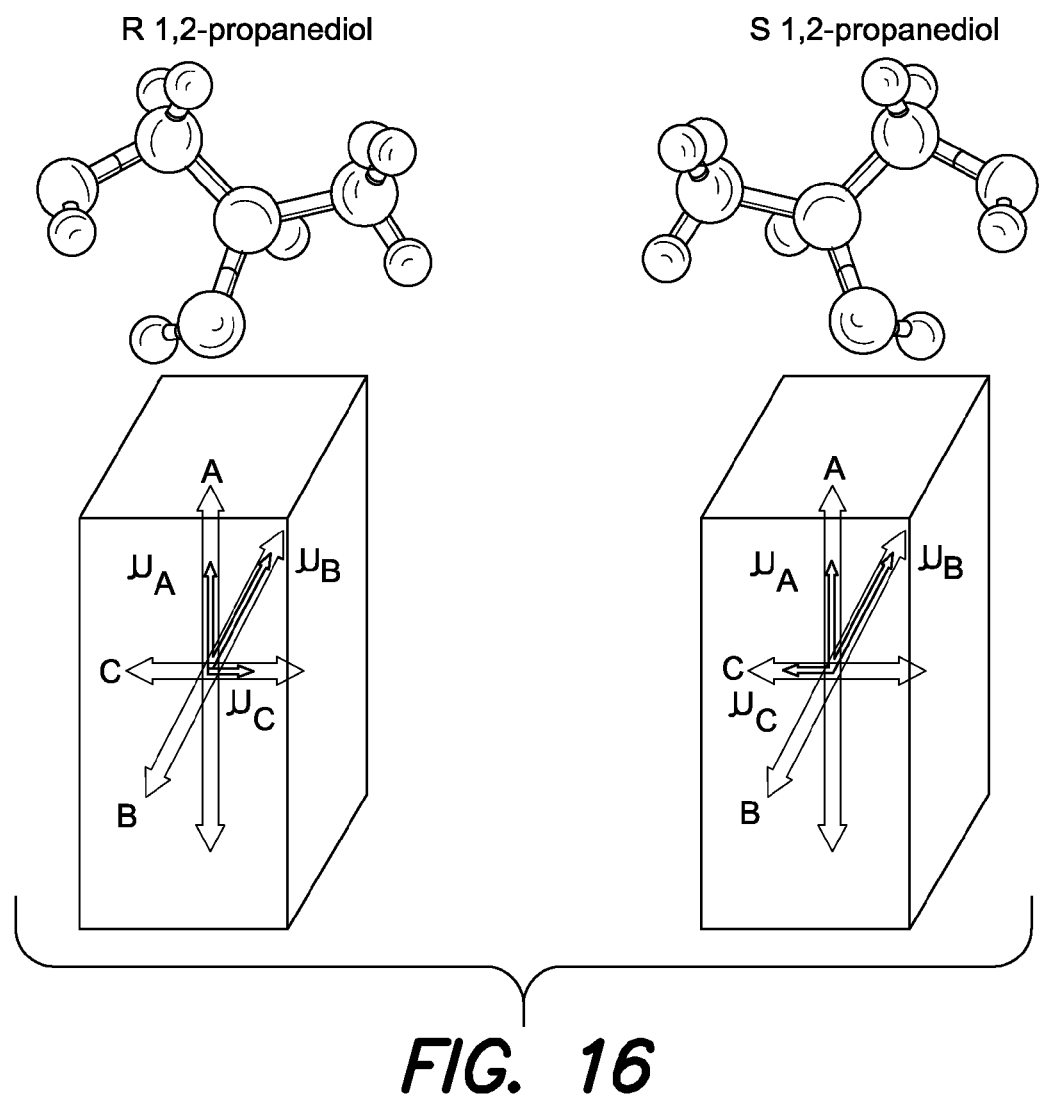
FIG. 16: Two enantiomers of chiral 1,2-propanediol. The Hamiltonian of 1,2-propanediol (or another chiral molecule) in an external electric field is enantiomer-dependent. Opposite enantiomers have substantially the same rotational constants A, B, and C, and substantially the same magnitude of dipole moment components $|\mu_a|$, $|\mu_b|$, and $|\mu_c|$, but the sign of the combined quantity $\mu_a\mu_b\mu_c$ is distinct for each enantiomer, independent of choice of axes. The displayed orientation of the molecules is for illustrative purposes.

The enantiomer-specific detection technique is demonstrated in this example using R-, S-, and racemic 1,2-propanediol. The two enantiomers of chiral 1,2-propanediol are shown in FIG. 16. This molecule was chosen as a prototype because the relevant molecular constants are well characterized and because it is readily available in enantio-pure form (Sigma Aldrich). At room temperature, molecules of the size of 1,2-propanediol or larger occupy a large number of quantum states, which dilutes the signal obtained from a single rotational level (e.g., more than about 5,000 occupied states for 1,2 propanediol). Cooling a sample reduces the number of occupied states and increases the resonant polarizability of the sample. In this example, a molecular gas is cooled using techniques set forth in D. Patterson and J. M. Doyle, Molecular Physics 110, 1757 (2012), the disclosure of which is incorporated herein by reference in its entirety. According to this cooling approach, warm molecules are injected into a cryogenic buffer gas cell thermally anchored to a closed-cycle pulse-tube refrigerator, cooling the molecules to a temperature of about 7 K.

Figure 17:
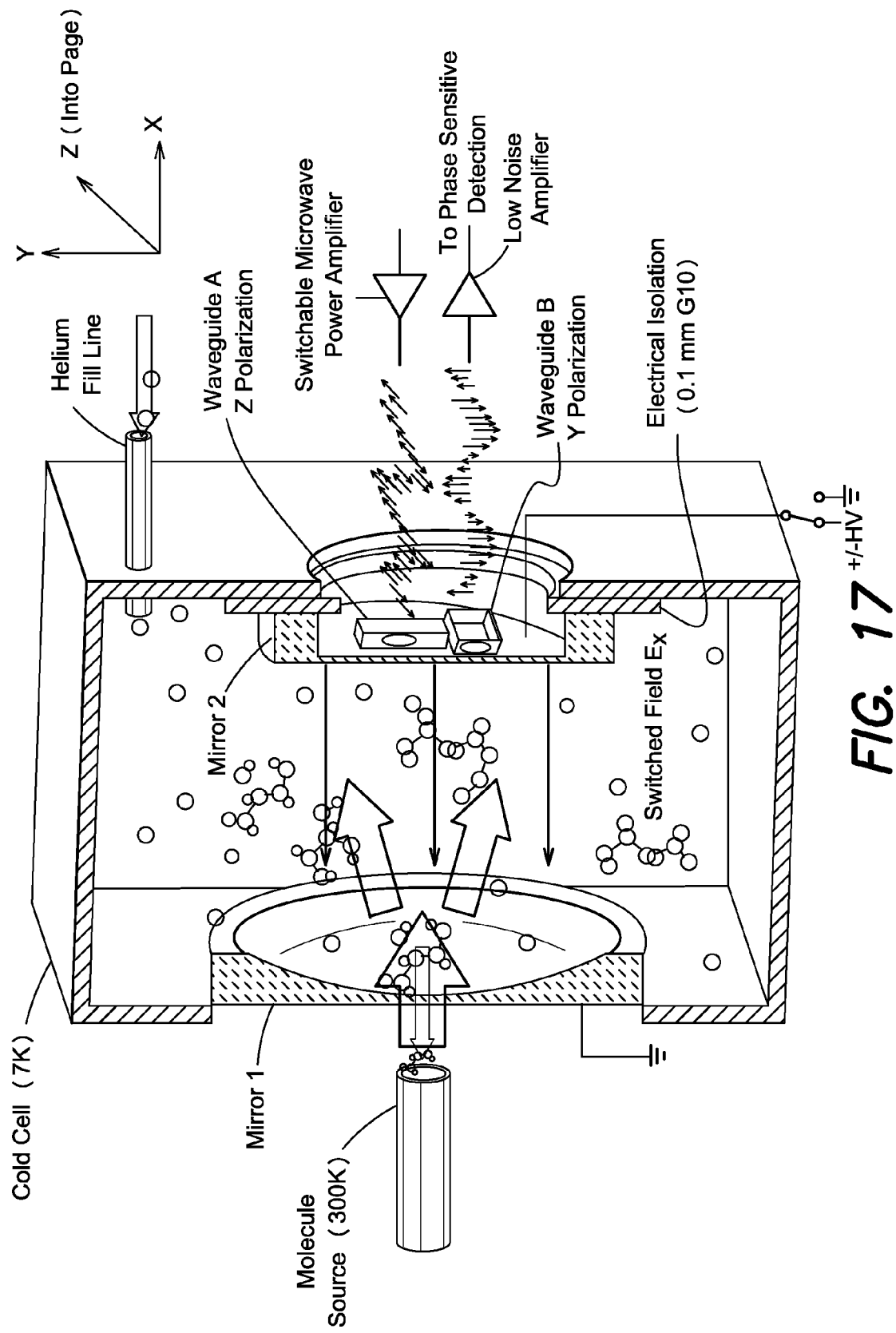
FIG. 17: A cryogenic buffer gas FTMW spectrometer to provide enantiomer-specific detection of 1-2 propanediol. Molecules are introduced into a cryogenic cell from a room temperature tube held close to an aperture in mirror 1. Microwave radiation is introduced using waveguides A and B via coupling apertures in mirror 2. Mirror 2 can be rapidly switched between ±500 volts and ground, applying a time-varying electric field in the x direction. The molecules are polarized initially in the z direction via a linearly polarized microwave pulse coupled from waveguide A. A resulting enantiomer-specific radiation is coupled out of a cavity via waveguide B, which is oriented to detect y-polarized microwaves.

A schematic of the experimental setup is shown in FIG. 17. Two walls of the cryogenic cell are formed by mirrors that define a tunable plano-concave Fabry-Perot microwave cavity, which is used to excite and detect the molecules. Each transverse and longitudinal spatial mode of the cavity supports two (degenerate) modes of orthogonal polarization. These modes can be separately addressed via waveguides attached to the planar mirror and coupled to the cavity via apertures (denoted as A and B in FIG. 17). A time-varying electric field $E_x$ parallel to a cavity axis can be applied by rapidly changing a voltage of the planar mirror ($V_{mirror}=\pm 500$ volts, $E_x=\pm 65$ V/cm); this voltage is controlled with high-voltage switches with a switching time of about 100 ns.

The experimental procedure is as follows. Molecules enter the cryogenic cell substantially continuously from a warm (about 300 K) feed tube. Upon entering the cell, the molecules begin to cool through collisions with a cold helium buffer gas. By the time the molecules diffuse into a central region of the cell, the molecules have reached a rotational temperature of about 7 K. The cold molecules remain in a gas phase as they diffuse through the cell for several milliseconds, until the molecules arrive at a cold cell wall, where the molecules freeze. A resulting detected signal primarily or substantially solely results from the cold, gas phase molecules. The experimental sequence of applied electric fields begins with the application of $E_x$. The cavity is then driven with a strong, linearly polarized microwave field with $E_z(t)=\hat{z} E_{mw} \cos(\omega t)$. The excitation frequency $\omega$ is tuned to the $|0_{00}\rangle \Rightarrow |1_{10}\rangle$ rotational transition of the ground-state conformation of 1,2-propanediol at about 12,212 MHz. The maximum magnitude of $E_z$ and the pulse length $\tau_{pulse}$ are adjusted to yield $|\Omega|\tau_{pulse} < \pi/2$ for all molecules, where $\Omega$ is the Rabi frequency. This microwave pulse induces an oscillating electric dipole polarization in the z direction in the molecular ensemble. About 200 ns after the end of the microwave pulse, the electric field $E_x$ is set to zero. $E_x$ is switched within about 200 ns—rapidly compared to the molecular decoherence rate but slowly compared to $\omega$. The change in $E_x$ induces a sizable fraction of the oscillating molecular dipole to radiate with y polarization.

Under these experimental conditions, the chirality-dependent y polarization has about 10% of the amplitude of the z polarization. The induced field $\in_y$, which has an enantiomer-dependent phase, is amplified and recorded. The molecules continue to radiate in this manner until the molecules re-thermalize rotationally via collisions with helium atoms, typically after about 5 μs. This completes one experimental cycle, which can be started again by turning $E_x$ back on. As in traditional FTMW spectroscopy, molecules in distinct parts of the cavity radiate constructively into the original cavity mode used to polarize the sample. This feature is retained here because modes with orthogonal polarization share a substantially identical spatial structure. The chirality-dependent signal $\in_y$ is proportional to $E_x E_z$. In order to cancel some systematic offsets in the detected microwave field, the change of sign of $\in_y$ with $E_x$ is exploited by subtracting traces taken with equal and opposite values of $E_x$.

Figure 18:
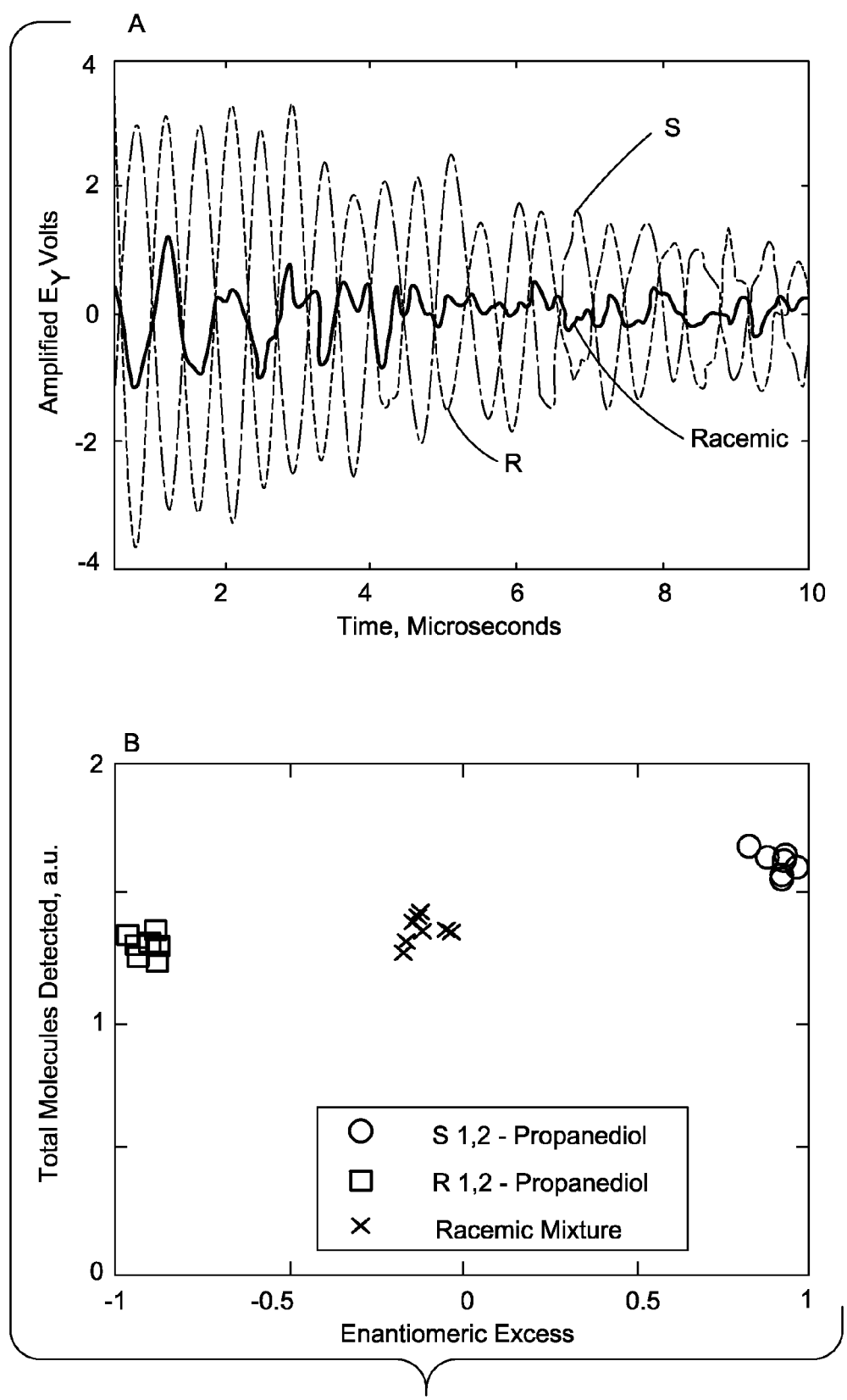
FIG. 18: A: Enantiomer-dependent, free induction decay traces for S-, R-, and racemic 1,2 propanediol. As predicted, opposite enantiomers show a 180 degree phase difference. B: Repeated measurements of enantiomeric excess (horizontal axis) and of total molecule number (vertical axis) for S-, R-, and racemic 1,2 propanediol. Each data point in B represents about 20 seconds of experimental time, and about 1 milligram of sample. Enantiomers are readily resolved.

FIG. 18 shows averaged signals for the S- and R-enantiomers of 1,2 propanediol, and a racemic mixture. Each signal represents the difference between a time trace taken with $E_x=+65$ V/cm and a trace taken with $E_x=-65$ V/cm. As predicted, the S- and R-enantiomers show a 180 degree phase shift. The opposite enantiomers and a racemic mixture are resolved with exceptionally high confidence. Hamiltonian integration calculations (shown in FIG. 5) are in excellent agreement with the experimental data. The induced field $\in_y$ scales as $\in_y \propto nT^{5/2}$, where n is the molecule density, and T is the temperature. This scaling suggests that a similar microwave analysis of a room temperature gas of chiral molecules at a modest vapor pressure of a few mTorr would have adequate sensitivity for enantiomer-specific analysis, making it particularly appealing as a next generation analysis technique.

Experimental Details:

In the experiments, a flow rate of about $1.5 \times 10^{18}$ helium atoms s$^{-1}$ into the cell provides an estimated in-cell helium density of about $10^{14}$ atoms cm$^{-3}$. About $5 \times 10^{17}$ 1,2 propanediol molecules s$^{-1}$ are sprayed towards the cell. The 1,2-propanediol density within the cell is estimated to be about $10^{12}$ molecules cm$^{-3}$. The experimental repetition rate of about 7 kHz is based on a maximum switching frequency of high voltage switches used; without this restriction, or when $E_x$ is set to zero, the rate is based on the molecular re-thermalization rate of about 200 kHz. The applied electric field $E_x$ is $\pm 65$ V/cm ($\pm 500$ volts on mirror 2). This high voltage is switched via Behlke HTS 151 high voltage MOSFET switches. The polarizing pulse is typically about 200 ns in duration, and a maximum microwave field $E_z$ is estimated to be about 0.5 V/cm from measurements of the Rabi frequency Ω. The cavity was run in a $T_{11}$ (n=6) mode, although another mode (e.g., $T_{00}$ mode) also can be used. Mirror 2 of the cavity was mounted on flexible bellows and could be moved axially by about 1 cm, tuning the cavity. This tuning was accomplished via three thermally isolating, flexible shafts connected via rotary feedthroughs to knobs outside the cavity. The aluminum cavity has a measured finesse of about 105, a length of about 8.1 cm, and a radius of curvature on its spherical mirror of about 22.5 cm. An input aperture for the molecules has a diameter of about 1.1 cm, and the coupling apertures A and B have diameters of about 0.8 cm. The waveguides connected via apertures A and B are WR-62, operating from about 12 GHz to about 18 GHz. $\in_y$ is detected after waiting about 2 μs for the cavity to ring down. The signal is amplified by a LNA (Pasternack PE1524) connected immediately outside the vacuum chamber with no protection diodes or switches. The amplified signal is mixed down to about 20 MHz, further amplified, and digitized by a fast signal averager (Agilent U1084). Each data point in FIG. 18 represents 140,000 averages, about 20 seconds of experimental time, and about 1 milligram of 1,2 propanediol.

The molecular constants used in this example are A=8572.055 MHz, B=3640.106 MHz, and C=2790.966 MHz for the rotational constants, and $\mu_a$=1.201 Debye, $\mu_b$=1.916 Debye, and $\mu_c$=0.365 Debye for the dipole moment components.

Sensitive Chiral Analysis Via Rotational Three Wave Mixing

This example sets forth a demonstration of chirality-induced three wave mixing in the microwave regime. Bulk three wave mixing is realized in a chiral environment, and provides a sensitive, species-selective probe of enantiomeric excess. Rotational transitions used have narrow resonances, and doubly resonant conditions, which are used to observe three wave mixing, provides extremely selective identification of enantiomers, even within a complex mixture of chiral molecular species. The technique is demonstrated here on 1,2-propanediol but can be used to sensitively measure enantiomeric excess in a broad class of chiral molecules, including 1,3-butanediol, carvone, limonene, and alaninol. In this example, sum-frequency generation, a type of three wave mixing, is demonstrated using two orthogonal resonant applied fields at frequencies $v_1$ and $v_2$ to induce mutually orthogonal radiation at the sum frequency $v_3=v_1+v_2$. The phase of this induced radiation changes sign with enantiomer, and the amplitude of this induced radiation yields a sensitive, quantitative measure of enantiomeric excess.

A z-polarized electric field $E_z$ at the frequency $v_1$ is used to drive a c-type transition, and a x-polarized electric field $E_x$ at the frequency $v_2$ is used to drive an a-type transition. These pulses induce y-polarized radiation $\in_y$ at the frequency $v_3=v_1+v_2$ from a b-type transition. In the weak-pulse limit, $\in_y$ is proportional to $\mu_a\mu_b\mu_c$, and changes sign with enantiomer. For an enantiopure sample, a predicted amplitude of $|\in_y|$ is comparable to the largest amplitude fields produced in "traditional" FTMW spectroscopy, while for a racemic sample $|\in_y|$=0.

Figure 19:
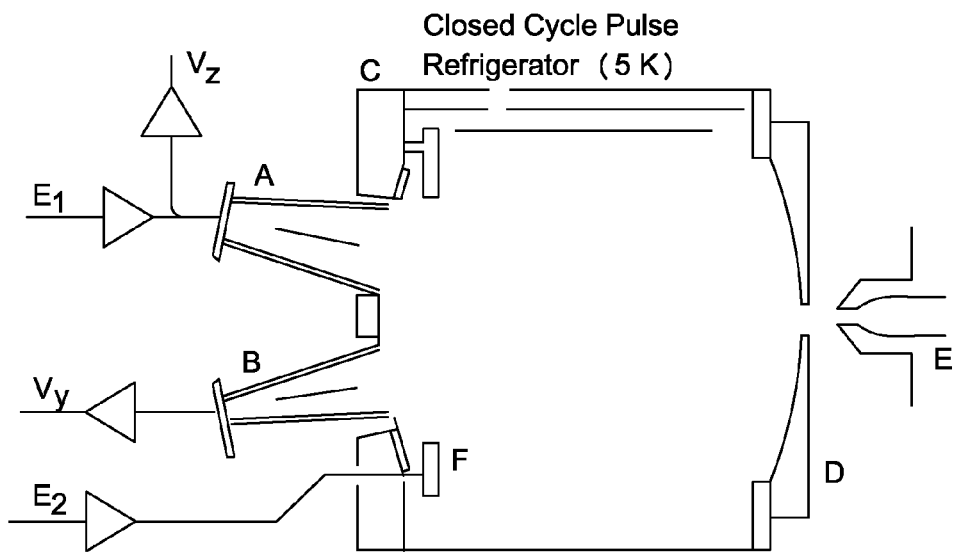
FIG. 19: An experimental setup to provide enantiomer-specific detection of 1-2 propanediol. A cold molecular sample is contained within a cold cell (about 6 K) anchored to a closed cycle pulse tube refrigerator. Molecules are introduced through a warm injection tube (about 300K) E through a 1 cm aperture in a mirror D, and cold helium is introduced via a fill line C. $E_z$ is applied by broadcasting z-polarized microwaves from horn A, which are reflected from the curved mirror D, and re-focused onto a second microwave horn B that is oriented to collect y-polarized microwaves. A substantially spatially uniform electric field $E_x$ can be applied between an electrode F and the mirror D. $v_1$ and $v_2$ can be varied from about 12-18 GHz, and $0 < v_3 < 200$ MHz.

A schematic of the experimental setup is shown in FIG. 19. The resonant electric fields $E_z$ and $E_x$ are applied in two orthogonal directions, while the induced radiation $\in_y$ is polarized in a third (y) orthogonal direction. $E_z$ is applied by broadcasting a pulse of microwaves through a cold gas sample from a z-polarized horn towards a spherical mirror. This mirror reflects and re-focuses the microwaves onto a second, y-polarized horn. The combination of the incident and reflected microwaves forms $E_z$. In front of the horns is an electrode, which can be independently charged, producing a x-polarized electric field $E_x$ between the electrode and the spherical mirror. The induced field $\in_y$ co-propagates with $E_z$, and is collected by the second microwave horn.

The experimental procedure is as follows. A substantially continuous stream of gas phase 1,2-propanediol molecules (Sigma-Aldrich) enter a cold cell (about 6 K) from a warm feed tube (about 300 K). The molecules cool through collisions with a cold helium buffer gas. The cold molecules remain in the gas phase for several milliseconds, until the molecules diffuse to a cold cell wall, where they freeze. The molecules are subjected to two substantially simultaneous 3 μsec duration electric field pulses $E_z$ and $E_x$. $E_z$ has the frequency $v_1$, which chirps from about 14,791→about 14,799 MHz, including the $|2_{11}\rangle\rightarrow|2_{21}\rangle$ transition in 1,2-propanediol at about 14,796 MHz. $E_x$ has the frequency $v_2$ of about 100.5 MHz tuned to the $|2_{21}\rangle\rightarrow|2_{20}\rangle$ transition, and has a strength $|E_x|\approx 1.5$ V/cm. The combination of pulses $E_z$ and $E_x$ resonantly drives molecules that are initially in the $|2_{11}\rangle$ state into a superposition $|\Psi\rangle=\alpha_1|2_{11}\rangle+\alpha_2|2_{21}\rangle\alpha_3|2_{20}\rangle$, with enantiomer-dependent complex coefficients $\alpha_i$. When all external fields are turned off, the ensemble radiates with nonzero polarization P in all three polarization directions. $P_z$ oscillates at $v_{12}$, $P_x$ oscillates at $v_{23}$, and $P_y$ oscillates at $v_{13}$. The induced microwave fields $\in_z$ and $\in_y$, corresponding to $P_z$ and $P_y$, are collected by the microwave horns and amplified, producing voltages $V_z$ and $V_y$, respectively.

$V_z$ and $V_y$ are recorded in a phase-repeatable way. To this end, $E_z$ is produced by single-sideband-modulating a free running carrier signal $S_1$ at a frequency $v_{S1}$ of about 14,760 MHz with a 31-39 MHz phase-repeatable chirp $C_1$, which is in turn generated by direct digital synthesis and is also used to phase-stably trigger a data acquisition system. $E_x$ is produced by a switched amplifier driven by a free running oscillator $S_2$ at the frequency $v_2$. $V_z$ is mixed with $S_1$ to produce a phase-repeatable, enantiomer-independent signal $V_1$ at a frequency $v_{12}$-$v_{S1}$ of about 35.8 MHz, while $V_y$ is mixed with $S_1$ and then with $S_2$ to produce a phase-repeatable, enantiomer-dependent signal $V_3$ at a frequency $v_{13}$-$v_{S1}$-$v_{S2}$, also at about 35.8 MHz. A fast signal averager (Agilent U1084A) triggered on the first rising edge of the baseband chirp $C_1$ digitizes and averages the signal. The entire pulse sequence is repeated at about 50 KHz, and many traces of $V_z$ and $V_y$ are accumulated and averaged.

The sign of $V_3$ is enantiomer-dependent; in a racemic sample, induced radiation from S- and R-enantiomers is opposite and no detectable signal is recorded. It should be noted that a racemic mixture typically will not radiate at the sum frequency $v_1+v_2$ despite any geometric errors in the device, as three wave mixing is strictly forbidden for a non-chiral bulk material. This zero background for a racemic sample provides an advantage of this technique, making it particularly sensitive in detecting slight enantiomeric excess.

Figure 20:
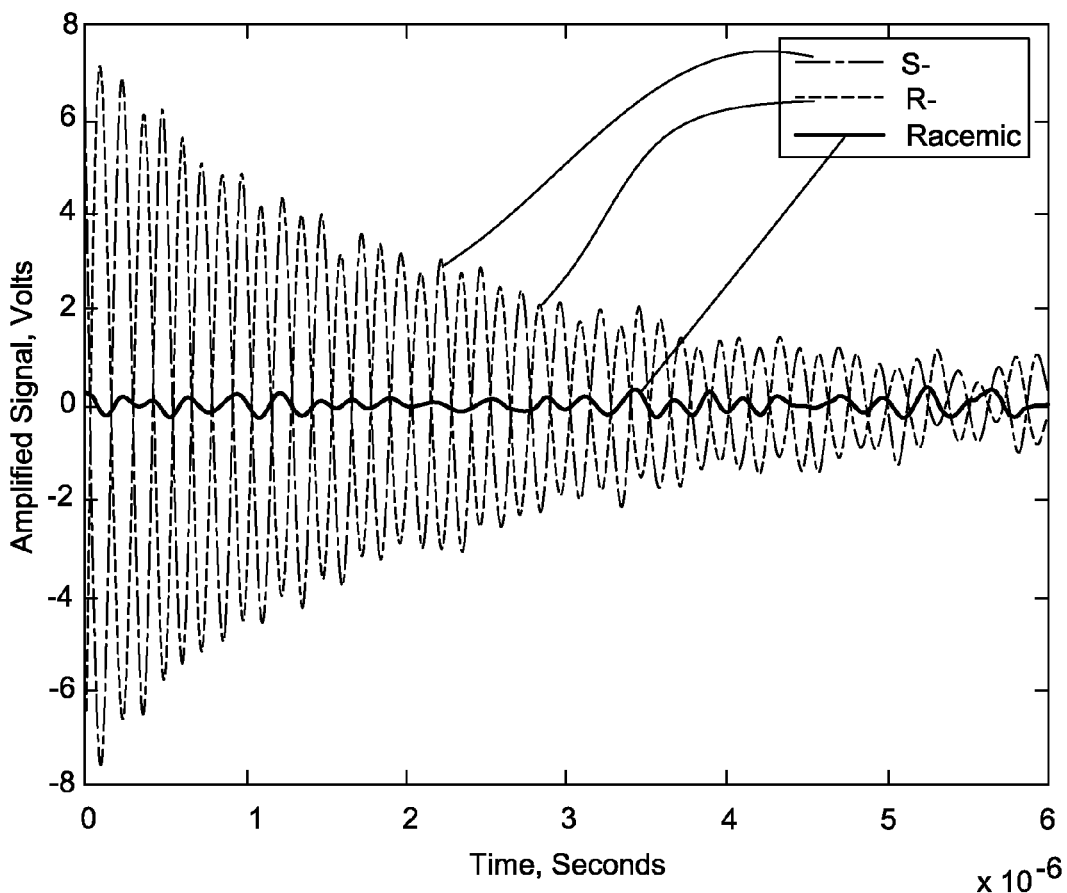
FIG. 20: A digitized signal for S-, R-, and racemic mixture. The signal is at about 14,896 GHz, but is digitized at an intermediate frequency of about 36 MHz and is shown here further mixed down to about 4 MHz. As expected, the signals change sign with enantiomer.
Figure 21:
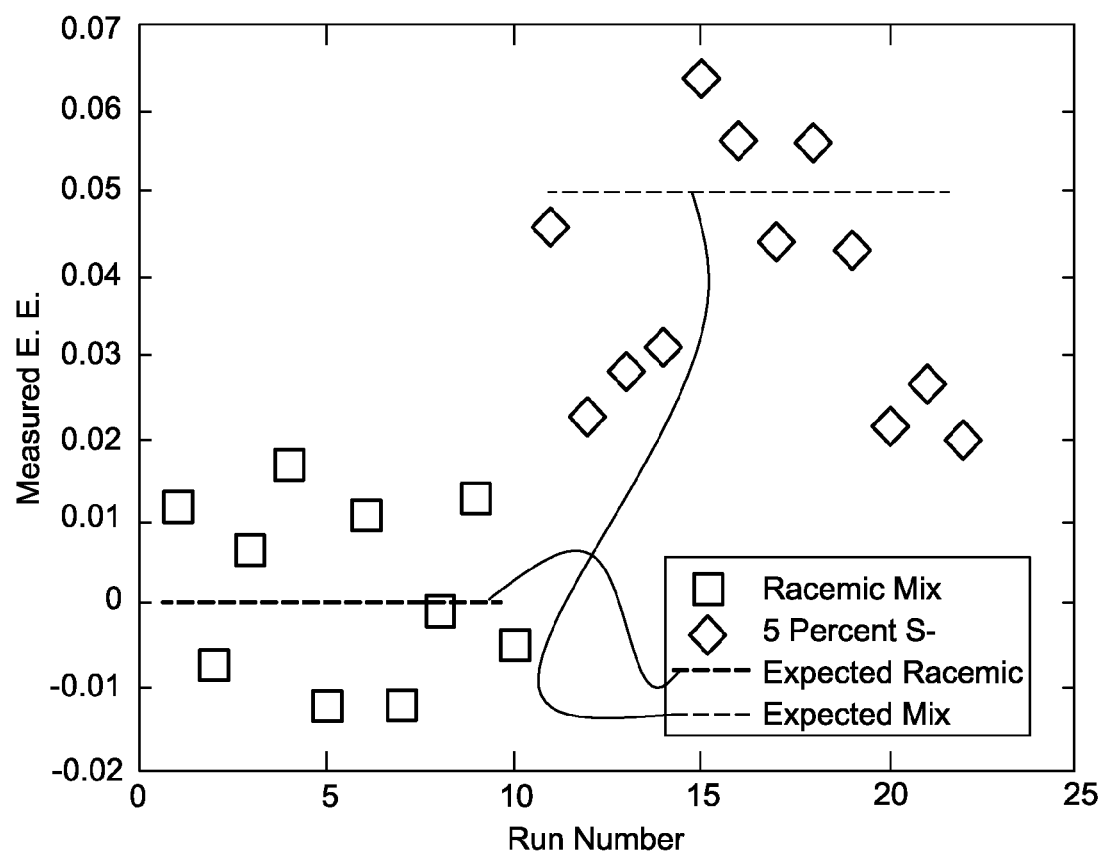
FIG. 21: Repeated measurements of enantiomeric excess for a racemic mixture (squares) and a prepared 0.05 enantiomeric excess mixture (diamonds). Each data point represents 2 million averages, consumes about 1 milligram of sample, and uses about 50 seconds of experimental time.

FIG. 20 shows a radiated signal for S-enantiomer, R-enantiomer, and a racemic mixture of 1,2-propanediol. As expected, the signal changes sign with enantiomer. FIG. 21 shows repeated measurements of a prepared 0.05 enantiomeric excess mixture and a racemic sample. The two samples can be readily resolved.

An embodiment of this disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of an embodiment of this disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment may be implemented using Java, C++, or other object-oriented programming language and development tools. Additional examples of computer code include encrypted code and compressed code. Moreover, an embodiment may be downloaded as a computer program product, which may be transferred from a remote computer (e.g., a server computer) to a requesting computer (e.g., a client computer or a different server computer) via a transmission channel. Another embodiment may be implemented in hardwired circuitry in place of, or in combination with, machine-executable software instructions.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, or process to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A spectrometer, comprising:
 a housing defining a volume into which an analyte gas is introduced, the analyte gas including a chiral component;
 a microwave generator coupled to the housing and configured to apply a microwave pulse to the analyte gas, the microwave pulse being polarized along a first direction;
 an electric field generator coupled to the housing and configured to apply a switched electric field to the analyte gas, the electric field being oriented along a second direction different from the first direction;
 a phase-sensitive microwave detector coupled to the housing and configured to detect an induced microwave emitted by the analyte gas, the induced microwave being polarized along a third direction different from the first direction and the second direction; and
 an analyzer coupled to the phase-sensitive microwave detector and configured to detect an enantiomer of the chiral component based on a phase of the induced microwave.

2. The spectrometer of claim 1, wherein the first direction, the second direction, and the third direction are substantially orthogonal to one another.

3. The spectrometer of claim 1, wherein the electric field generator is configured to activate the electric field after application of the microwave pulse and before detection of the induced microwave.

4. The spectrometer of claim 1, wherein the electric field generator is configured to deactivate the electric field after application of the microwave pulse and before detection of the induced microwave.

5. The spectrometer of claim 1, wherein the electric field generator is configured to activate the electric field substantially in parallel with application of the microwave pulse.

6. The spectrometer of claim 1, wherein the housing includes a set of reflectors to define a microwave cavity.

7. The spectrometer of claim 1, wherein the microwave generator is configured to apply the microwave pulse as a broadband chirped pulse.

8. A spectrometer, comprising:
 a housing defining a volume into which an analyte gas is introduced, the analyte gas including a chiral component;
 a microwave generator coupled to the housing and configured to apply a microwave pulse to the analyte gas, the microwave pulse configured to induce a first polarization along a first direction;
 an electric field generator coupled to the housing and configured to apply a switched electric field to the analyte gas, the electric field configured to induce a second polarization along a second direction different from the first direction;
 a set of microwave detectors coupled to the housing and configured to detect the first polarization and the second polarization; and
 an analyzer coupled to the set of microwave detectors and configured to detect a chirality of the chiral component based on a phase of the second polarization.

9. The spectrometer of claim 8, wherein the first direction is substantially orthogonal to the second direction.

10. The spectrometer of claim 8, wherein the housing includes a first reflector and a second reflector to define a microwave cavity.

11. The spectrometer of claim 10, wherein a first microwave detector of the set of microwave detectors is coupled to the cavity via a first aperture formed in the first reflector, and a second microwave detector of the set of microwave detectors is coupled to the cavity via a second aperture formed in the second reflector.

12. The spectrometer of claim 8, wherein the analyzer is configured to detect an enantiomeric excess of the chiral component based on a magnitude of the second polarization.

13. A spectrometer, comprising:
 a housing defining a volume into which an analyte gas is introduced, the analyte gas including a chiral component;
 a first generator coupled to the housing and configured to apply a first pulse to the analyte gas, the first pulse being polarized along a first direction;
 a second generator coupled to the housing and configured to apply a second pulse to the analyte gas, the second pulse being polarized along a second direction different from the first direction;

a phase-sensitive detector coupled to the housing and configured to detect an induced radiation emitted by the analyte gas, the induced radiation being polarized along a third direction different from the first direction and the second direction; and an analyzer coupled to the phase-sensitive detector and configured to detect an enantiomer of the chiral component based on a phase of the induced radiation.

14. The spectrometer of claim 13, wherein the first direction, the second direction, and the third direction are substantially orthogonal to one another.

15. The spectrometer of claim 13, wherein the first generator and the second generator are configured to apply the first pulse and the second pulse sequentially.

16. The spectrometer of claim 13, wherein the first generator and the second generator are configured to apply the first pulse and the second pulse substantially simultaneously.

17. The spectrometer of claim 13, wherein the first generator is configured to apply the first pulse at a higher frequency relative to the second pulse.

18. The spectrometer of claim 13, wherein the first generator is configured to apply the first pulse as a first microwave pulse.

19. The spectrometer of claim 18, wherein the second generator is configured to apply the second pulse as a second microwave pulse.

20. The spectrometer of claim 13, wherein the analyzer is configured to detect an enantiomeric excess of the chiral component based on a magnitude of the induced radiation.

* * * * *